(12) United States Patent
Davis et al.

(10) Patent No.: US 10,204,706 B2
(45) Date of Patent: Feb. 12, 2019

(54) USER INTERFACE FOR OPTIMIZING ENERGY MANAGEMENT IN A NEUROSTIMULATION SYSTEM

(75) Inventors: Jon P. Davis, St. Michael, MN (US); Steven M. Goetz, North Oaks, MN (US); Nathan A. Torgerson, Andover, MN (US); Ashish Singal, Blaine, MN (US); Lynn A. Davenport, Roseville, MN (US); Rajeev M. Sahasrabudhe, Maple Grove, MN (US); Shyam Gokaldas, New Brighton, MN (US); Joel A. Anderson, Brookly Park, MN (US); Leroy L. Perz, Buffalo, MN (US); Scott E. Straka, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1159 days.

(21) Appl. No.: 12/771,475

(22) Filed: Apr. 30, 2010

(65) Prior Publication Data
US 2011/0106213 A1    May 5, 2011

Related U.S. Application Data

(60) Provisional application No. 61/256,229, filed on Oct. 29, 2009.

(51) Int. Cl.
*A61N 1/08* (2006.01)
*G16H 40/63* (2018.01)
*G06F 19/00* (2018.01)

(52) U.S. Cl.
CPC ............. *G16H 40/63* (2018.01); *G06F 19/00* (2013.01)

(58) Field of Classification Search
CPC .... A61N 1/3605; A61N 1/37247; A61N 1/36; A61N 1/3708
(Continued)

(56) References Cited

U.S. PATENT DOCUMENTS

| 4,556,061 A | 12/1985 | Barreras et al. |
| 5,137,020 A | 8/1992 | Wayne et al. |

(Continued)

FOREIGN PATENT DOCUMENTS

| EP | 0160801 A2 | 11/1985 |
| WO | 0105466 A1 | 1/2001 |

(Continued)

OTHER PUBLICATIONS

U.S. Appl. No. 12/815,095, filed Jun. 14, 2010, Michaels et al.
(Continued)

*Primary Examiner* — Alyssa M Alter
(74) *Attorney, Agent, or Firm* — Shumaker & Sieffert, P.A.

(57) ABSTRACT

In one aspect, a programmer for an implantable medical device comprises a user interface that receives user input corresponding to one or more selected stimulation therapy parameters for delivering stimulation therapy to a patient with the implantable medical device and presents an energy consumption estimate of a power source based on the selected stimulation therapy parameters; and a processor that determines one or more programming options that, if selected, would alter the selected stimulation therapy parameters and reduce the energy consumption estimate. The user interface presents at least one of the programming options to reduce the energy consumption estimate to the user with an indication that user selection of one or more of the presented (Continued)

programming options would alter the selected stimulation therapy parameters to reduce energy consumption of the implantable medical device.

28 Claims, 12 Drawing Sheets

(58) Field of Classification Search
USPC .......................................................... 607/59
See application file for complete search history.

(56) References Cited

U.S. PATENT DOCUMENTS

| | | | |
|---|---|---|---|
| 5,325,041 | A | 6/1994 | Briggs |
| 5,344,431 | A | 9/1994 | Merritt et al. |
| 5,369,364 | A | 11/1994 | Renirie et al. |
| 5,391,193 | A | 2/1995 | Thompson |
| 5,769,873 | A | 6/1998 | Zadeh |
| 6,016,448 | A | 1/2000 | Busacker et al. |
| 6,108,579 | A | 8/2000 | Snell et al. |
| 6,141,583 | A | 10/2000 | Pape et al. |
| 6,191,557 | B1 | 2/2001 | Gray et al. |
| 6,198,253 | B1 | 3/2001 | Kurle et al. |
| 6,366,809 | B1 | 4/2002 | Olson et al. |
| 6,400,988 | B1 | 6/2002 | Gurewitsch |
| 6,534,954 | B1 | 3/2003 | Plett |
| 6,584,355 | B2 | 6/2003 | Stessman |
| 6,648,823 | B2 | 11/2003 | Thompson |
| 6,671,552 | B2 | 12/2003 | Merritt et al. |
| 6,748,273 | B1 | 6/2004 | Obel et al. |
| 6,820,019 | B1 | 11/2004 | Kelly et al. |
| 6,885,894 | B2 | 4/2005 | Stessman |
| 6,901,293 | B2 | 5/2005 | Rogers et al. |
| 7,123,964 | B2 | 10/2006 | Betzold et al. |
| 7,142,923 | B2 | 11/2006 | North et al. |
| 7,167,756 | B1 | 1/2007 | Torgerson et al. |
| 7,177,690 | B2 | 2/2007 | Woods et al. |
| 7,191,005 | B2 | 3/2007 | Stessman |
| 7,194,308 | B2 | 3/2007 | Krig et al. |
| 7,215,999 | B1 | 5/2007 | Shahandeh et al. |
| 7,221,977 | B1 | 5/2007 | Weaver et al. |
| 7,239,146 | B2 | 7/2007 | James et al. |
| 7,450,991 | B2 | 11/2008 | Smith et al. |
| 7,469,161 | B1 | 12/2008 | Gandhi et al. |
| 7,542,801 | B2 | 6/2009 | Rogers et al. |
| 7,711,426 | B2 | 5/2010 | Armstrong et al. |
| 8,108,160 | B2 | 1/2012 | Liu et al. |
| 8,116,998 | B2 | 2/2012 | Hess |
| 2003/0065366 | A1 | 4/2003 | Merritt et al. |
| 2004/0039424 | A1 | 2/2004 | Merritt et al. |
| 2005/0102005 | A1 | 5/2005 | Krig et al. |
| 2005/0177206 | A1 | 8/2005 | North et al. |
| 2005/0277994 | A1 | 12/2005 | McNamee et al. |
| 2006/0111854 | A1 | 5/2006 | Plett |
| 2006/0111870 | A1 | 5/2006 | Plett |
| 2006/0212277 | A1 | 9/2006 | Hansen et al. |
| 2007/0150018 | A1 | 6/2007 | Betzold et al. |
| 2007/0179547 | A1 | 8/2007 | Armstrong et al. |
| 2007/0179548 | A1 | 8/2007 | Armstrong et al. |
| 2007/0179549 | A1 | 8/2007 | Russie |
| 2008/0097544 | A1 | 4/2008 | Gandhi et al. |
| 2008/0177345 | A1 | 7/2008 | Schmidt et al. |
| 2008/0306569 | A1 | 12/2008 | Tobacman |
| 2009/0099625 | A1* | 4/2009 | Crowley et al. ................ 607/59 |
| 2009/0182517 | A1 | 7/2009 | Gandhi et al. |
| 2009/0276015 | A1 | 11/2009 | Rondoni et al. |
| 2010/0076704 | A1 | 3/2010 | Liu et al. |
| 2011/0031938 | A1 | 2/2011 | Ishikawa |
| 2011/0133690 | A1 | 6/2011 | Crane |

FOREIGN PATENT DOCUMENTS

| | | |
|---|---|---|
| WO | 0249718 A1 | 6/2002 |
| WO | 2004091697 A1 | 10/2004 |
| WO | 2008038202 A2 | 4/2008 |
| WO | 2009055203 A1 | 4/2009 |
| WO | 2009078905 A1 | 6/2009 |
| WO | 2009091407 A2 | 7/2009 |
| WO | 2009134473 A1 | 10/2010 |

OTHER PUBLICATIONS

Battery and Energy Technologies, State of Charge (SOC) Determination, Electropedia, 2005, 6 pages.

Office action for U.S. Appl. No. 12/815,095, dated Aug. 22, 2013, 18 pages.

Response to Office Action dated Aug. 22, 2013, from U.S. Appl. No. 12/815,095, filed Nov. 12, 2013, 7 pp.

Final Office Action from U.S. Appl. No. 12/815,095, dated Jan. 27, 2014, 22 pp.

Response to Final Office Action dated Jan. 27, 2014, from U.S. Appl. No. 12/815,095, filed Apr. 24, 2014, 15 pp.

Office Action from U.S. Appl. No. 12/815,095, dated May 22, 2014, 26 pp.

Maybeck, "Stochastic models, estimation and control," vol. 1, Chapter 1, Academy Press, May 28, 1979, 19 pp.

Notice of Allowance from U.S. Appl. No. 12/815,095, dated Oct. 7, 2014, 20 pp.

Response to Office Action dated May 22, 2014 from U.S. Appl. No. 12/815,095, filed Aug. 21, 2014, 14 pp.

* cited by examiner

USER INTERFACE FOR OPTIMIZING ENERGY MANAGEMENT IN A NEUROSTIMULATION SYSTEM

This application claims the benefit of U.S. Provisional Application No. 61/256,229, filed Oct. 29, 2009, the entire content of which is incorporated by reference herein.

TECHNICAL FIELD

The disclosure relates to medical devices and, more particularly, to medical devices for delivery of electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse amplitude (voltage or current), pulse width and pulse rate. A set of parameter values may be referred to as a stimulation program. A program group may include multiple programs. Multiple programs in a program group may be delivered on a simultaneous, time-interleaved, or overlapping basis.

SUMMARY

Generally, this disclosure describes techniques for indicating an energy consumption estimate of a stimulation therapy delivered by an electrical stimulator as parameters of the therapy are being selected by a user. The ability to view an indication of an energy consumption estimate for selected parameters may permit a user to actively balance therapeutic benefit with energy consumption. For example, greater energy efficiency, i.e., lower energy consumption, may be desired to increase longevity of a rechargeable battery, and thereby reduce patient burden associated with frequent recharge sessions. Similarly, for a non-rechargeable battery, greater energy efficiency may be desired to increase device longevity between implant and explant. An indication of an energy consumption estimate associated with one or more therapy parameters, such as electrode combination, electrode polarity, stimulation amplitude, pulse width, pulse rate, or duty cycle, may permit a user to select therapy parameters that support therapeutic efficacy while limiting energy consumption. A programmer for an electrical stimulator may show a summary of energy consumption for an active therapy and, in some cases, present programming options for selection by a user to reduce energy consumption. The programmer may also guide the selection of new parameters by predicting their likely impact on energy consumption.

In one example, the disclosure is directed to a programmer for an implantable medical device comprising a user interface that receives user input corresponding to one or more selected stimulation therapy parameters for delivering stimulation therapy to a patient with the implantable medical device and presents an energy consumption estimate of a power source based on the selected stimulation therapy parameters; and a processor that determines one or more programming options that, if selected, would alter the selected stimulation therapy parameters and reduce the energy consumption estimate. The user interface presents at least one of the programming options to reduce the energy consumption estimate to the user with an indication that user selection of one or more of the presented programming options would alter the selected stimulation therapy parameters to reduce energy consumption of the implantable medical device.

In another example, the disclosure is directed to a method comprising receiving, with a user interface of a programmer for an implantable medical device, user input corresponding to one or more selected stimulation therapy parameters for delivering stimulation therapy to a patient with the implantable medical device; presenting, with the user interface, an energy consumption estimate of a power source based on the selected stimulation therapy parameters; determining, with a processor of the programmer, one or more programming options that, if selected, would alter the selected stimulation therapy parameters and reduce the energy consumption estimate; and presenting, with the user interface, at least one of the programming options to reduce the energy consumption estimate to the user with an indication that user selection of one or more of the presented programming options would alter the selected stimulation therapy parameters to reduce energy consumption of the implantable medical device.

In another example, the disclosure is directed to a system comprising means for delivering a stimulation therapy to a patient; means for receiving user input corresponding to one or more selected stimulation therapy parameters for delivering the stimulation therapy to the patient; means for determining one or more programming options that, if selected, would alter the selected stimulation therapy parameters and reduce an energy consumption estimate for the stimulation therapy; and means for presenting at least one of the programming options to reduce the energy consumption estimate to the user with an indication that user selection of one or more of the presented programming options would alter the selected stimulation therapy parameters to reduce the energy consumption estimate.

In another example, the disclosure is directed to a computer-readable medium comprising instructions that, upon execution, cause a processor to determine an energy consumption estimate for selected stimulation therapy parameters for delivering medical therapy to a patient with an implantable medical device; determine one or more programming options that, if selected, would alter selected stimulation therapy parameters and reduce the energy consumption estimate, present, via a user interface, at least one of the programming options to reduce the energy consumption estimate to a user with an indication that user selection of one or more of the presented programming options would alter the selected stimulation therapy parameters to reduce energy consumption of the implantable medical device.

The details of one or more aspects of the disclosure are set forth in the accompanying drawings and the description below. Other features, objects, and advantages will be apparent from the description and drawings, and from the claims.

DETAILED DESCRIPTION

The examples of this disclosure may provide the user with the ability to dynamically perceive the effect of electrical stimulation therapy parameter changes on an energy consumption estimate of stimulation therapy and the tradeoff between the effectiveness of the therapy applied with the burden on the patient, e.g., in terms of time between recharge sessions in the case of a rechargeable battery, or time between implant and explant in the case of a non-rechargeable primary battery. Additionally, examples of this disclosure also may provide the user with the ability to see a summary of energy consumption for an active therapy session, guide a user in selecting new parameters by predicting their likely impact on energy consumption, and present therapy parameter programming options to improve energy consumption.

Figure 1:
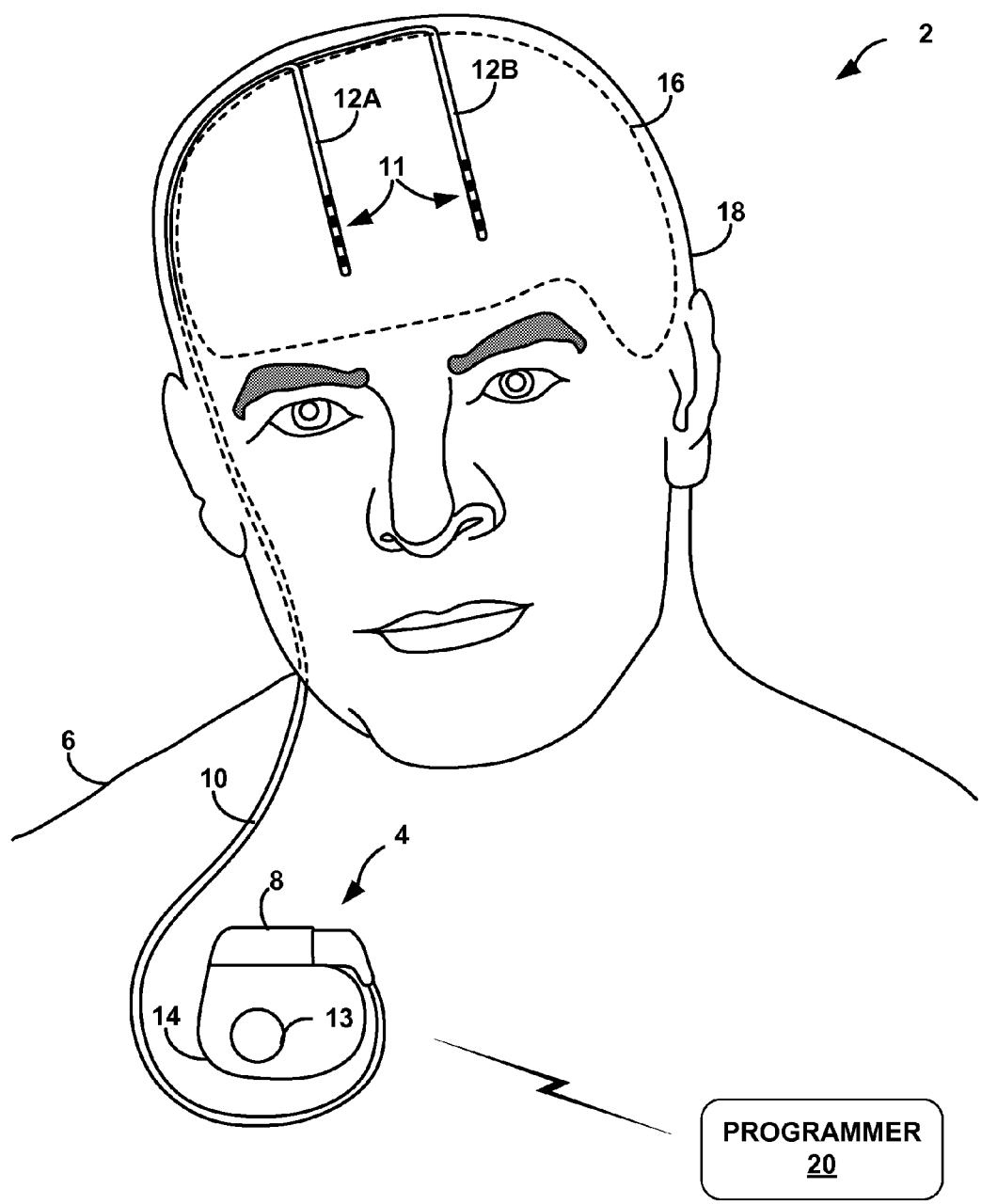
FIG. 1 is a conceptual diagram illustrating an example therapy system that includes an implantable stimulator coupled to a stimulation lead.

FIG. 1 is a conceptual diagram illustrating an example system 2 that may be used to deliver stimulation therapy to patient 6. Patient 6 ordinarily, but not necessarily, will be a human. Therapy system 2 includes implantable stimulator 4 that delivers electrical stimulation to patient 6 via one or more implantable electrodes, such as electrodes 11 on implantable medical lead 10. The implantable electrodes may be deployed on one or more implantable medical leads, such as implantable medical lead 10, and in some cases on a can electrode. In other examples an implantable stimulator may be a leadless stimulator including electrodes on an external surface of an external housing of the implantable stimulator. Although FIG. 1 shows a fully implantable stimulator 4, techniques described in this disclosure may be applied to external stimulators having electrodes deployed via percutaneously implantable leads with a patch electrode or other indifferent electrode attached externally to serve as the can or case. One or more of the electrodes may be located on a housing 14, i.e., "can" or "case," of the implantable stimulator 4. In addition, in some cases, implantable electrodes may be deployed on a leadless stimulator.

The electrical stimulation may be in the form of controlled current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs.

In the example illustrated in FIG. 1, implantable stimulator 4 is implanted within a subcutaneous pocket in a clavicle region of patient 6. Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, or a portion of the housing 14. In other examples, electrode 13 may be formed by an electrode on a dedicated short lead extending from housing 14. As a further alternative, housing electrode 13 could be provided on a proximal portion of one of the leads carrying electrodes 11. The proximal portion may be closely adjacent to housing 14, e.g., at or near a point at which lead 10 is coupled to the housing, such as adjacent to a lead connection header 8 of the housing. In another example, a patch electrode or other indifferent electrode may be attached externally to serve as the can or case.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. Lead 10 traverses from the implant site of implantable stimulator 4 along the neck of patient 6 to cranium 18 of patient 6 to access brain 16. Lead segments 12A and 12B may be implanted within the right and left hemispheres, respectively, in order to deliver electrical stimulation to one more regions of brain 16, which may be selected based on the patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B are implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the occipital nerve or to the visual cortex of brain 16 in order to reduce or eliminate migraine headaches afflicting patient 6. As illustrated by these examples, the target therapy delivery site generally depends upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also includes a programmer 20, which may be a clinician or patient programmer. Programmer 20 may be a handheld computing device that permits a user to program stimulation therapy for patient 6 via a user interface, e.g., using input keys and a display. For example, using programmer 20, the clinician may specify stimulation parameters, i.e., create programs, for use in delivery of stimulation therapy. Programmer 20 may support telemetry (e.g., radio frequency (RF) telemetry) with implantable stimulator 4 to download programs and, optionally, upload operational or physiological data stored by implantable stimulator 4. In this manner, a user, such as the patient or the clinician, may periodically interrogate implantable stimulator 4 to evaluate efficacy and, if necessary, modify the programs or create new programs. In some examples, clinician programmer transmits programs to patient programmer in addition to or instead of implantable stimulator 4. A clinician programmer may be used more extensively in programming and downloading therapy, and may have more capabilities, such as, for example, the ability to change more therapy parameters than a patient programmer.

Patient programmer may be a handheld computing device, and may include a display and input keys to allow patient 6 to interact with patient programmer and implantable stimulator 4. In this manner, patient programmer provides patient 6 with a user interface for control of the stimulation therapy delivered by implantable stimulator 4. For example, patient 6 may use patient programmer to start, stop or adjust electrical stimulation therapy. In particular, patient programmer may permit patient 6 to adjust stimulation parameters of a program such as electrode combination, electrode polarities, duration, current or voltage amplitude, pulse width and pulse rate. Patient 6 may also select a program, e.g., from among a plurality of stored programs, as the present program (or one of a plurality of programs in a program group) to control delivery of stimulation by implantable stimulator 4.

Programmer 20 may be used to graphically define desired stimulation field(s) within zones on or adjacent to one or more leads, and generate the current stimulation required to create the stimulation field. In particular, programmer 20 may be used for translating one or more user input stimulation zones into a set of electrodes for delivering electrical stimulation therapy to a patient, determining the variable electrical stimulation contributions of each electrode to the zone, and determining amplitudes of electrical stimulation when using zone-based programming. Programmer 20 may also be used for graphically representing the stimulation zone and receiving input from a user that manipulates the shape and position of the zone. Programmer 20 may also be used to graphically define therapy by specifying current levels for each electrode.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer may be used to create programs, and assemble the programs into program groups. A patient programmer may also be used to adjust stimulation parameters of one or more programs of a program group, and select a program group, e.g., from among a plurality of stored program groups, as the current program group to control delivery of stimulation by implantable stimulator 4.

In some examples, implantable stimulator 4, a clinician programmer or a patient programmer may be used to estimate the energy level consumed by implantable stimulator 4 in real-time. The user of the programmer may set parameters for the active therapy session, and based on the set parameters, an estimation of energy consumption may be updated accordingly. For example, the estimation of energy consumption may be based on a real-time measurement of energy consumption for the selected therapy parameters by implantable stimulator 4 or a model that estimates energy consumption for the selected therapy parameters. The energy consumption may be displayed in terms of the remaining life of a primary cell, or the amount of time left until a rechargeable cell may need to be recharged to ensure uninterrupted therapy delivery to the patient, or may be represented directly in coulombs/hour or in watts, or in a unitless measure (e.g., 0 to 10), or in other ways. Stimulator 4 may include measurement circuitry for measuring actual energy consumption by a selected therapy program, and provide the measurement, e.g., by wireless telemetry, to the external programmer 20. Programmer 20 may use the measurement to present an indication of energy consumption for a given program or set of therapy parameters to the user. The user may then associate the indicated energy consumption with the selected program or one or more selected parameters to evaluate energy consumption and determine whether it may be desirable to adjust the parameters or make a different selection of parameters or programs. The indication may be expressed in a variety of ways, including textual or graphical indications of actual energy consumption levels.

In addition, as described in further detail below, programmer 20 may present one or more programming options to reduce the energy consumption estimate to the user with an indication that user selection of one or more of the presented programming options would alter the selected stimulation therapy parameters to reduce energy consumption of the implantable medical device.

Implantable stimulator 4 and programmer 20 may communicate via cables or a wireless communication, as shown in FIG. 1. When both are used, clinician programmer and patient programmer may, for example, communicate via wireless communication with implantable stimulator 4 using RF telemetry techniques known in the art. Clinician programmer and patient programmer may also communicate with each other using any of a variety of local wireless communication techniques, such as RF communication according to the 802.11 or Bluetooth specification sets, infrared communication, e.g., according to the IrDA standard, or other standard or proprietary telemetry protocols. Programmer 20 may include a transceiver to facilitate bi-directional communication with implantable stimulator 4.

Generally, system 2 delivers stimulation therapy to patient 6 in the form of constant current or voltage waveforms or constant current or voltage pulses. The shapes of the pulses may vary according to different design objectives. In the case of current-based stimulation, implantable stimulator 4 regulates current that is sourced or sunk by one or more electrodes, referred to as regulated electrodes. In some examples, one of the electrodes may be unregulated. In such configurations, either the housing electrode or a lead electrode may be the unregulated electrode.

A source current may refer to a positive current that flows out of an electrode, e.g., from a regulated current source via a regulated current path to surrounding tissue, or from a reference voltage via an unregulated current path. A sink current may refer to a negative current that flows into an electrode, e.g. from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current. An unregulated current path can source or sink current approximately equal to this net difference.

Figure 2:
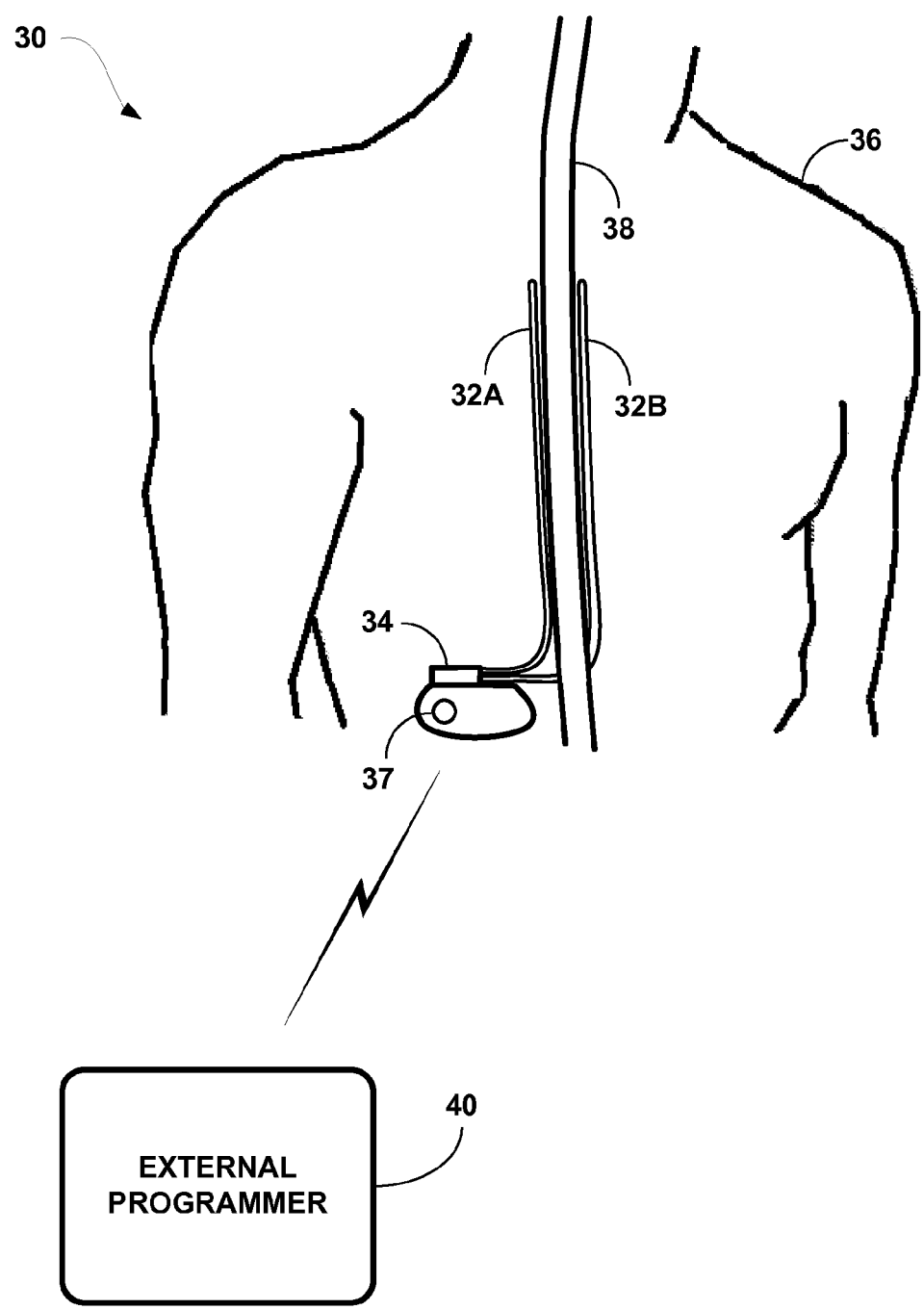
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from implantable stimulator 34 to spinal cord 38 via one or more electrodes (not shown) carried by, i.e., located on, implantable medical leads 32A and 32B (collectively "leads 32") as well as the housing of implantable stimulator 34, e.g., housing electrode 37. System 30 and, more particularly, implantable stimulator 34 may operate in a manner similar to implantable stimulator 4 (FIG. 1). That is, in a current-based example, implantable stimulator 34 delivers controlled current stimulation pulses or waveforms to patient 36 via one or more regulated stimulation electrodes. Alternatively, implantable stimulator 34 may be configured to deliver constant voltage pulses. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to implantable stimulator 34 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses. Some of the electrodes may be electrode pads on a paddle lead, circular (i.e., ring), electrodes surrounding the body of leads 32, conformable electrodes, cuff electrodes, segmented electrodes, or any other type of electrodes capable of forming unipolar, bipolar or multi-polar electrode configurations.

In an implantable stimulator, such as, for example, an implantable stimulator of FIG. 1 or FIG. 2, the stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current.

A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 34 perceives the interruption of pain signals as a reduction in pain and, therefore, efficacious therapy.

In some examples, implantable stimulator 34 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 34 may interleave pulses or other signals according to the different programs of a program group, e.g., cycle through the programs, to simultaneously treat different symptoms or different body regions, or provide a combined therapeutic effect. In such examples, clinician programmer may be used to create programs, and assemble the programs into program groups. A patient programmer may also be used to adjust stimulation parameters of one or more programs of a program group, and select a program group, e.g., from among a plurality of stored program groups, as the current program group to control delivery of stimulation by implantable stimulator 34.

Further, in some examples, separate programs may be selected for a set of program slots. Each slot may be associated with one or more programs that form therapy options for the slot, and each slot may target a different symptom or area of pain. One program may be selected from each slot, where the selection of a program in one slot is independent of the programs selected in other slots. In other words, therapy is defined by multiple slots, and each slot is defined by selection of one of a plurality of programs serving as therapy options designated for the slot. In applying stimulation therapy, programs for different slots may be delivered on an interleaved or rotating basis. In some examples, the programs in the slots may be delivered in fast succession. In the example of stimulation therapy for chronic pain, the programs in the slots may be delivered in fast succession such that a patient experiences near-constant paresthesia from the combined effect of each of the programs simultaneously.

With reference to FIG. 2, a user, such as a clinician or patient 36, may interact with a user interface of external programmer 40 to program stimulator 34. Programming of stimulator 34 may refer generally to the generation and transfer of commands, programs, or other information to control the operation of the stimulator. For example, programmer 40 may transmit programs, parameter adjustments, program selections, group selections, or other information to control the operation of stimulator 34, e.g., by wireless telemetry.

In some cases, external programmer 40 may be characterized as a physician or clinician programmer, if it is primarily intended for use by a physician or clinician. In other cases, external programmer 40 may be characterized as a patient programmer, if it is primarily intended for use by a patient. In general, a physician or clinician programmer may support selection and generation of programs by a clinician for use by stimulator 34, whereas a patient programmer may support adjustment and selection of such programs by a patient during ordinary use.

Whether programmer 40 is configured for clinician or patient use, programmer 40 may communicate with implantable stimulator 34 or any other computing device via wireless communication. Programmer 40, for example, may communicate via wireless communication with implantable stimulator 34 using RF telemetry techniques known in the art. Programmer 40 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 40 may also communicate with another programming or computing device via exchange of removable media, such as magnetic or optical disks, or memory cards or sticks. Further, programmer 40 may communicate with other programming devices via remote telemetry techniques known in the art, communicating via a local area network (LAN), wide area network (WAN), public switched telephone network (PSTN), or cellular telephone network, for example.

Programming of stimulator 34 may also include graphically defining a desired stimulation field(s) within zones on or adjacent to one or more leads or electrodes, and generating, via a programmer, the current stimulation required to create the stimulation field. Programming of stimulator 34 may also include translating one or more user input stimulation zones into a set of electrodes for delivering electrical stimulation therapy to a patient, and a set of parameters such as pulse current amplitudes associated with such electrodes. Programming may further include manipulating the shape and position of the zone, including behaviors of the zone while moving and when colliding with other zones or system interlocks. As the stimulation zone is sized, moved, or shaped, the programmer may automatically compute updated electrode selections and parameters for delivery of stimulation indicated by the stimulation zone.

While the techniques of this disclosure are described in terms of a zone-based stimulation system, it should be understood that the techniques described herein are not limited to zone-based therapy. For example, the techniques of this disclosure may be applicable to other methods of defining and applying stimulation therapy, such as, for example, a system where electrodes may be programmed individually.

In accordance with the techniques described in this disclosure, programming of stimulator 34 may also include adjusting a therapy to be delivered by the stimulator 34 and receiving real-time feedback from the programmer 40 regarding, for example, the energy consumption and the remaining life of the source powering the stimulator 34. The feedback may also include, for example, the perceived efficacy of the therapy, or options that may improve the efficacy and/or the energy consumption of the stimulator 34. Adjusting the therapy may include, for example, changing parameters associated with a therapy such as stimulation amplitude including current and/or voltage amplitude, pulse width, pulse rate, the number of activated leads or electrodes in a group or program, electrode combination, electrode polarity, the power output of each of the leads in a group or program, the number of active programs in a group, and the programs selected for individual slots. In one example, multiple parameters may be adjusted individually to achieve the desired therapy, and the corresponding energy consumption may be evaluated in real-time and indicated to the user via programmer 40. In another example, some parameters may be adjusted relative to each other to achieve a defined desired level of energy consumption. For example, programmer 40 may present a selection mechanism that may range from maximum energy consumption and minimum amplitude to maximum amplitude and minimum energy consumption, with a user being able to choose a setting within the range based on the desired energy consumption of the therapy.

Although the disclosure generally refers to implantable electrical stimulators for purposes of illustration, techniques described in this disclosure may be also used with other types of implantable medical devices, including implantable fluid delivery devices, such as insulin pumps, intra-thecal drug delivery pumps, or other devices that deliver medication or other fluids via one or more fluid delivery elements such as catheters. Such devices may provide fluid delivery therapy for chronic pain, diabetes, or any of a variety of other disorders. In each case, the device may include one or more therapy delivery elements such as one or more catheters implanted within a therapy region. In some cases, a pump may be fully implantable or may be an external device coupled to one or more percutaneously implanted catheters that extend into a therapy region. In some examples, the techniques of this disclosure may be also used with external neural stimulators, such as, for example, those used for "trialing" therapies and/or devices with a patient prior to implantation. Accordingly, description of implantable stimulators is provided for purposes of illustration and should not be considered limiting of the techniques as broadly described in this disclosure.

Figure 3:
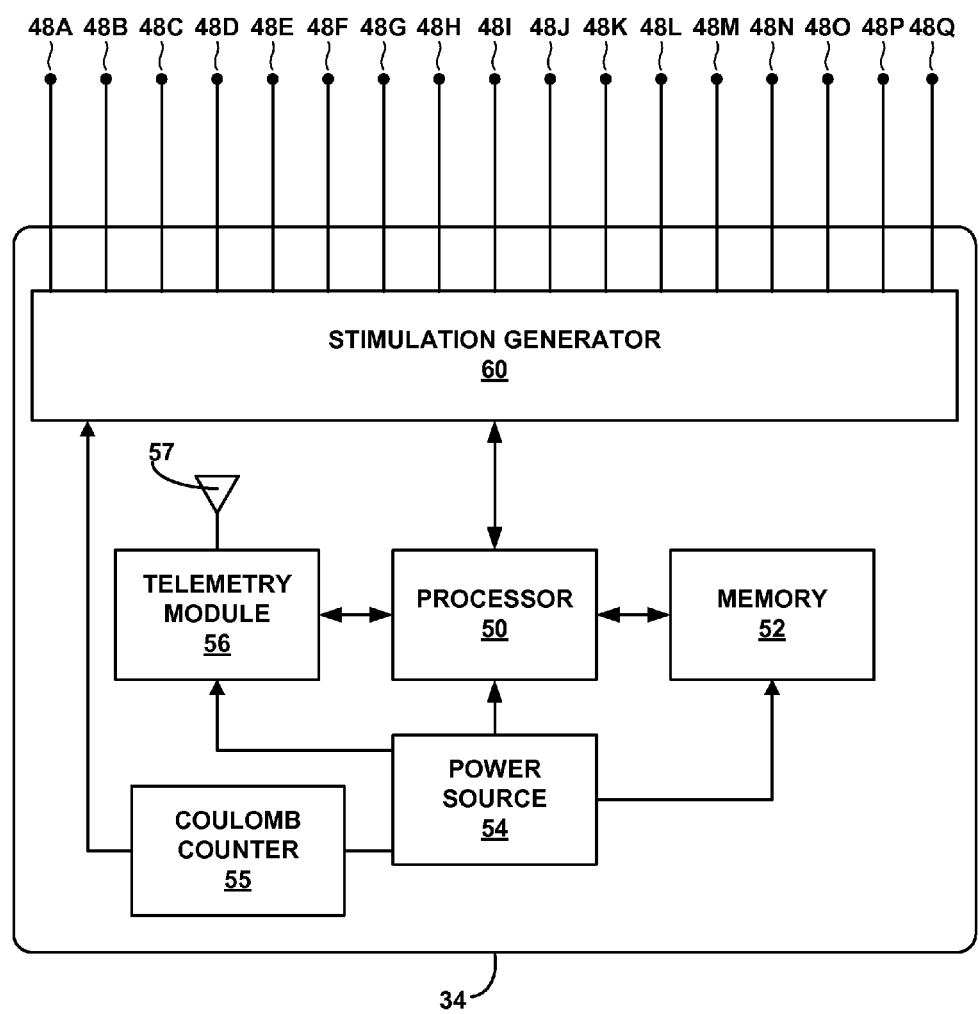
FIG. 3 is a block diagram illustrating various example components of an implantable electrical stimulator.

FIG. 3 is a block diagram illustrating various components of an example implantable stimulator 34. Although the components shown in FIG. 3 are described in reference to implantable stimulator 34, the components may also be included within implantable stimulator 4 shown in FIG. 1 and used within system 2. In the example of FIG. 3, implantable stimulator 34 includes processor 50, memory 52, power source 54, coulomb counter 55, telemetry module 56, antenna 57, and a stimulation generator 60. Implantable stimulator 34 is also shown in FIG. 3 coupled to electrodes 48A-Q (collectively "electrodes 48"). Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of implantable stimulator 34, e.g., to provide a common or ground electrode or a housing anode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 4. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 4, such as stimulation generator 60, processor 50, memory 52, telemetry module 56, and power source 54.

Housing electrode 48Q may be configured for use as an anode to source current substantially simultaneously with current sourced by one or more other electrodes 48A-48P to form a unipolar or omnipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q. Any of a variety of electrode arrangements such as unipolar, bipolar, multipolar, or omnipolar arrangements may be used to deliver stimulation. Accordingly, discussion of particular arrangements is provided for purposes of illustration which should not be considered limiting of the techniques broadly described in this disclosure.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Information stored on the memory 52 may include a patient profile and information regarding therapy that the patient 6 had previously received. Storing such information may be useful for subsequent treatments such that, for example, a clinician may retrieve the stored information to determine the therapy applied to the patient during his/her last visit. The information may be modified and updated by a user of a programmer. The information stored in the memory 52 may be an image captured and downloaded into the implantable stimulator 34 by a programmer, such as clinician programmer 20 by wireless telemetry. As an example, the image may be obtained during an in-clinic programming session, and may show, for example, lead configuration and placement within a therapy region targeted by one or more leads implanted in the therapy region. Information stored in memory 52 may be retrieved by the programmer to effectively deliver therapy in subsequent sessions. The therapy region could be any of several anatomical regions of patient in which one or more leads may be implanted for delivery of therapy, including the spinal cord, the occipital region, the brain, the pelvic floor, the heart, the gastrointestinal tract, one or more limbs, or the like.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with current amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs. Processor 50 may control stimulation generator 60 based on parameters specified by programs downloaded from an external programmer such as, for example, programmers 20 or 40. An external programmer, such as a clinician or patient programmer, may also specify that processor 50 should select one or more programs or program groups that have been downloaded to the implantable stimulator.

Upon selection of a particular program group, e.g., in response to a command received by wireless telemetry from an external programmer 20, 40, processor 50 may control stimulation generator 60 to deliver stimulation according to the programs in the groups, e.g., simultaneously or on a time-interleaved basis. A group may include a single program or multiple programs. Alternatively, as mentioned previously, multiple programs may be selected for separate program slots. As also mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. A program may be defined directly, by selecting parameters and electrodes, or by zone-based programming, in which parameters and electrodes are automatically determined by the programmer in response to manipulation or positioning of stimulation zones.

Stimulation generator 60 is electrically coupled to electrodes 48A-P via conductors of the respective lead, such as lead 12 in FIG. 1 or leads 32 in FIG. 2, in implementations in which electrodes 48A-P are carried by, or located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads of the IMD. Housing electrode 48Q may be configured for use as an anode to source current substantially simultaneously with one or more electrodes, e.g., any of electrodes 48A-48P, on one or more leads configured for use as anodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50.

For example, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Stimulation generator 60 may be configured to deliver stimulation using one or more of electrodes 48A-P as stimulation electrodes, e.g., anodes, while substantially simultaneously delivering stimulation using housing electrode 48Q as a stimulation electrode, e.g., anode. The anodes on the lead(s) and the housing may be used to deliver stimulation in conjunction with one or more cathodes on the lead(s). As one illustration, an electrode combination selected for delivery of stimulation current may comprise an anode on the IMD housing, and anode on a lead, and a cathode on the same lead or a different lead. In other examples, the electrode combination may include multiple anodes and/or multiple cathodes on one or more leads in conjunction with at least one anode on the IMD housing.

Telemetry module 56 may include a radio frequency (RF) transceiver to facilitate bi-directional communication between implantable stimulator 34 and programmer 20. Telemetry module 56 may include an antenna 57 that may take on a variety of forms. For example, antenna 57 may be formed by a conductive coil or wire embedded in a housing associated with medical device 4. Alternatively, antenna 57 may be mounted on a circuit board carrying other components of implantable stimulator 34 or take the form of a circuit trace on the circuit board. In this way, telemetry module 56 may facilitate communication with programmer 20 in FIG. 1 or external programmer 40 in FIG. 2, to receive, for example, new programs or program groups, or adjustments to programs or program groups.

Power source 54 may be a non-rechargeable primary cell battery or a rechargeable battery and may be coupled to power circuitry. However, the disclosure is not limited to examples in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4. In some examples, power requirements may be small enough to allow stimulator 4 to utilize patient motion at least in part and implement a kinetic energy-scavenging device to trickle charge a rechargeable battery. A voltage regulator may generate one or more regulated voltages using the battery power.

In accordance with this disclosure, power source 54 may be evaluated by processor 50 to determine the longevity of the power source. The longevity may be qualitative and/or quantitative. In an example, the longevity of the power source 54 may be expressed in terms of the amount of time before a recharge or replacement of the power source 54 may be needed, or the amount of time until the power source 54 is completely depleted. The processor 50 may evaluate the longevity of power source 54 based on the information it receives from programmer 40 via telemetry module 56. The processor 50 may receive from programmer 40 information such as, for example, parameters and programs associated with therapy to be delivered to the patient. Processor 50 may estimate energy consumption associated with delivery of therapy according to such parameters and/or programs and transmit an indication of energy consumption to an external programmer 20, 40 for use in presenting energy consumption indication to a user.

In one example, processor 50 may use measurements from coulomb counter 55 to estimate energy consumption. Coulomb counter 55 directly measures charge consumed by specified stimulation parameters. Coulomb counter 55 is positioned at the output of power source 54 to accurately reflect the amount of current or charge (e.g., in coulombs) being delivered to stimulation generator 60 during therapy. If coulomb counter 55 is configured to measure coulombs, the actual amount of charge transferred to the electrodes may be determined. If current is measured, the integral of current over the time that stimulation is delivered will yield the number of milliamp-hours. In either event, using the relationship that one coulomb equals approximately 0.00027778 amp-hours, the charge delivered by the power supply may be determined as an indication of current consumption when particular therapy parameters are selected.

Measurements by coulomb counter 55 may be used instantly by processor 50 to estimate energy consumption for applied therapy parameters. In addition, measurements by coulomb counter 55 may also be stored in memory, e.g., memory 52 of implantable stimulator 34 or memory of a programmer for use in future energy consumption estimates. Because actual energy consumed by a set of particular stimulation parameters is dependent on a variety of factors unique for a particular patient and stimulation system, lead coulomb counter 55 facilitates accurate energy consumption estimates. Factors that can effect energy consumption for a given set of stimulation parameters may even change over time after implantation of implantable stimulator 34 within a patient. For example, factors that can effect energy consumption for a given set of stimulation parameters include, but are not limited to: lead placement, lead migration, lead conductor impedance, resistances between selected electrodes and tissue growth within a patient. Coulomb counter 55 allows processor 50 to account for changes to one or more of these factors over time in energy consumption estimates.

Figure 4:
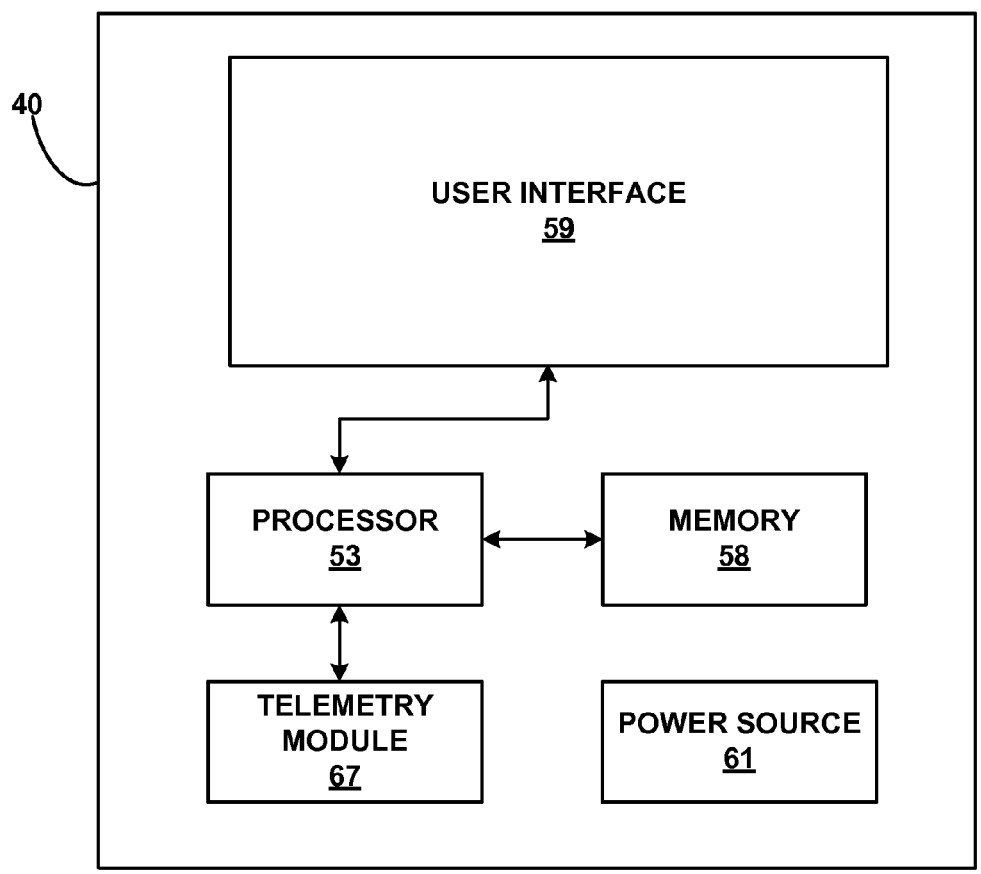
FIG. 4 is a block diagram illustrating various example components of an external programmer for an implantable electrical stimulator.

FIG. 4 is a functional block diagram illustrating various components of an external programmer 40 for an implantable stimulator 14. Although the components shown in FIG. 4 are described in reference to external programmer 40, the components may also be included within a clinician programmer or a patient programmer, or programmer 20 shown in FIG. 1. As shown in FIG. 4, external programmer 40 includes processor 53, memory 58, telemetry module 67, user interface 59, and power source 61. In general, processor 53 controls user interface 59, stores and retrieves data to and from memory 58, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 58 may store instructions that cause processor 53 to provide various aspects of the functionality ascribed to external programmer 40 herein. Memory 58 may include any fixed or removable magnetic, optical, or electrical media, such as RAM, ROM, CD-ROM, magnetic disks, EEPROM, or the like. Memory 58 may also include a removable memory portion that may be used to provide memory updates or increases in memory capacities. A removable memory may also allow patient data to be easily transferred to another computing device, or to be removed before programmer 40 is used to program therapy for another patient. Memory 58 may also store information that controls operation of implantable stimulator 4, such as therapy delivery values.

A clinician or patient 36 interacts with user interface 59 in order to, for example, manually select, change or modify programs, e.g., by adjusting voltage or current amplitude, adjusting pulse rate, adjusting pulse width, or selecting different electrode combinations, polarities, or configurations, and may provide efficacy feedback or view stimulation data. User interface 59 may include a screen and one or more input hard and/or soft key buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

A clinician or patient 36 may graphically define one or more desired stimulation regions using interface 59. In particular, user interface 59 may be used for graphically representing the stimulation zone and receiving input from a user that manipulates the shape and position of the zones and/or adjusting values associated with electrodes individually. Using the graphically defined stimulation zone or zones, programmer 40 may automatically define various parameter settings selected to deliver stimulation therapy that corresponds substantially to the stimulation zone or zones.

The user interface 59 may also display information indicating the energy consumption of stimulation therapy delivered by the electrical stimulator, e.g., as parameters of the therapy are being selected by a user. The ability to view an indication of energy consumption for selected parameters may permit a user to actively balance therapeutic benefit with energy consumption. For example, greater energy efficiency may be desired to increase longevity of a rechargeable battery, and thereby reduce patient burden associated with frequent recharge sessions. Similarly, for a non-rechargeable battery, greater energy efficiency may be desired to increase device longevity between implant and explant. An indication of energy consumption associated with various therapy parameters, such as electrode combination, electrode polarity, stimulation amplitude, pulse width, pulse rate, or duty cycle, may permit a user to select therapy parameters that support therapeutic efficacy while limiting energy consumption. A programmer for an electrical stimulator may show a summary of energy consumption for an active therapy and, in some cases, present programming options for selection by a user to reduce energy consumption. For example, the programmer may communicate to the user the longevity of the power source 54 of the stimulator 34 when the stimulator delivers a selected or defined therapy by the user, as will be described in more detail below. The energy consumption estimate, e.g., such as a longevity indication, may be based on actual measured energy consumption, calculated or predicted energy consumption, or both.

In one example, the graphical representation of the lead may be used to select particular electrodes forming an electrode combination, and assign current or voltage amplitudes to the electrodes. In some cases, the programmer may be configured to permit a user to define one or more stimulation zones with respect to a set of electrodes depicted by the graphical representation of the lead, and permit the user to manipulate the stimulation zone, e.g., by sizing, shaping or repositioning the zone. As the zone is manipulated, the programmer may automatically update the selection of electrodes associated with the zone, and adjust stimulation intensity (e.g., pulse current or pulse voltage) representing stimulation intensity contributions of the electrodes (e.g., as source or sink electrodes) in forming a stimulation field according to the stimulation zone. As the zone is manipulated, the power source longevity indicator may be updated to reflect the effect of the selected therapy zone on the life of the power source, in accordance with this disclosure.

Telemetry module 67 allows the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 67 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 67 which may be coupled to an internal antenna or an external antenna. Telemetry module 67 may be similar to telemetry module 56 of implantable stimulator 34. In accordance with this disclosure, programmer 40 may communicate with stimulator 34, via telemetry module 56 to retrieve information for determining an energy consumption estimate of stimulator 34. The energy consumption estimate may be displayed to a user via user interface 59. For example, the programmer 40 may communicate with stimulator 34, via telemetry module 56 to retrieve the amount of "charge" on power source 54 and/or the amount of energy consumed while program is running, and processor 53 of programmer 40 may determine the longevity of the power source 59 based on information or selections entered by a user.

Programmer 40 may also be configured to communicate with another computing device via wireless communication techniques, or direct communication through a wired, e.g., network, connection. Examples of local wireless communication techniques that may be employed to facilitate communication between programmer 40 and another computing device include RF communication based on the 802.11 or Bluetooth specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor energy remaining within a battery in the programmer 40. In this manner, user interface 59 may provide a current battery level indicator or low battery level indicator when the battery needs to be replaced or recharged. In some cases, power source 61 may be capable of estimating the remaining time of operation using the current battery.

Figure 5:
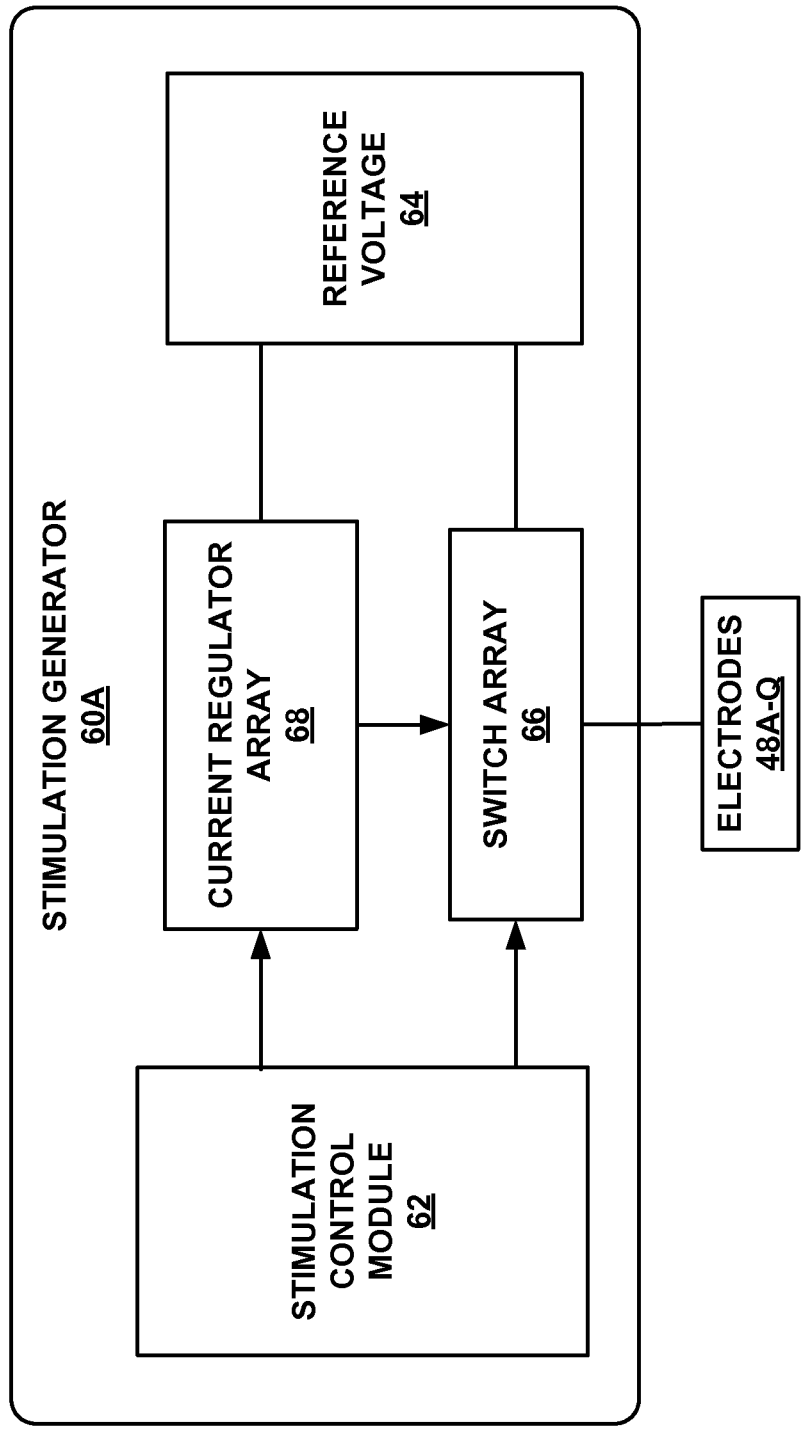
FIG. 5 is a block diagram illustrating various components of an example electrical stimulation generator for use in the implantable electrical stimulator of FIG. 3.

FIG. 5 is a block diagram illustrating various components of an example stimulation generator 60A. Stimulation generator 60A may be used with an implantable stimulator, e.g., to perform the functions of stimulation generator 60 as described with reference to FIGS. 1-3. Although described with respect to implantable stimulator 4, stimulation generator 60A may also be used for implantable stimulator 34, or other types of stimulators. In the example of FIG. 5, stimulation generator 60A is selectively, e.g., based on a signal from processor 50 (FIG. 3), configured to deliver constant current stimulation pulses to patient 6 via various electrode combinations. However, the disclosure is not limited to examples in which regulated current pulses are delivered. In other examples, stimulation generator 60A may provide continuous, regulated current waveforms, rather than regulated current pulses. In still other examples, stimulation generator 60A may deliver combinations of continuous waveforms and pulses, or selectively deliver either continuous waveforms or pulses. Stimulation generator 60A may generate either constant current-based or constant voltage-based stimulation in the form of pulses or continuous waveforms.

In the example illustrated in FIG. 5, stimulation generator 60A includes stimulation control module 62, reference voltage source 64, switch array 66, and current regulator array 68. Reference voltage source 64 may provide operating power to current regulator array 68, and may include a regulated voltage that sets the level of the reference voltage. As shown in FIG. 5, reference voltage source 64 may be coupled to provide operating power for the current regulator array 68 and provide a reference voltage for connection to electrodes 48A-48Q for an unregulated mode of electrode operation. In other examples, however, the voltage levels of the reference voltage and the operating voltage provided to regulate current source array 68 may be different.

Stimulation control module 62 forms a stimulation controller that controls switch array 66 and current regulator array 68 to deliver stimulation via electrodes 48A-48Q. Stimulation control module 62 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 62 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an implantable stimulator 4 or 34 for use by stimulation control module 62.

Current regulator array 68 includes a plurality of regulated current sources or sinks Again, a current regulator may function as either a current source or sink, or be selectively configured to operate as either a source or a sink. For convenience, however, the term "current regulator" may be used in some instances to refer to either a source or sink. Hence, each of the current regulators in current regulator array 68 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each switch of switch array 66 couples a corresponding one of electrodes 48 to either a corresponding bidirectional current regulator of current regulator array 68 or to reference voltage 64. In some examples, stimulation control module 62 selectively opens and closes switches in switch array 66 to configure a housing electrode, e.g., electrode 48Q, and one or more of electrodes 48A-48P on one or more leads as regulated electrodes by connection to regulated current sources or sinks in current regulator array 68. In other examples, stimulation control module 62 may selectively open and close switches in switch array 66 to configure either the housing electrode, e.g., electrode 48Q, or an electrode on the lead as an unregulated electrode by connection to reference voltage 64. In addition, stimulation control module 62 may selectively control individual regulated current sources or sinks in current regulator array 68 to deliver stimulation current pulses to the selected electrodes.

Reference voltage 64 may be a high or low voltage supplied by a regulated power source, depending on whether an electrode is programmed to be an unregulated source (high voltage rail) or unregulated sink (low voltage rail). Hence, reference voltage 64 may produce high and low reference voltages for selective coupling to unregulated, reference electrodes as needed given the selected electrode configuration. A regulated power source may produce one or more regulated voltage levels for use as reference voltage 64 and for use as a power rail for current regulator array 68. Again, although the same reference voltage 64 is coupled to current regulator array 68 in FIG. 5, different voltage levels could be used for the reference voltage coupled to switch array 66 and the operating voltage level provided to the regulated current source array. A regulated power source may generate the regulated voltages from voltages provided by a power source 54 (FIG. 3), such as a battery.

Stimulation control module 62 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with reference voltage 64. As previously described, in some examples, two or more regulated stimulation electrodes 48 may be intentionally programmed to deliver different amounts of current such that the regulated electrodes produce an unbalanced current distribution.

To provide individual control of electrodes 48 as either regulated electrodes or as unregulated, reference electrodes, stimulation control module 62 controls operation of switch array 66, and current regulator array 68. When stimulation is delivered to patient 6, for the example of current pulses, stimulation control module 62 controls switch array 66 to couple selected stimulation electrodes for a desired electrode combination to respective current regulators of current regulator array 68 or to reference voltage 64, as needed. Stimulation control module 62 controls the regulated bidirectional current sources of current regulator array 68 coupled to regulated electrodes to source or sink specified amounts of current. For example, stimulation control module 62 may control selected current sources or sinks to on a pulse-by-pulse basis to deliver current pulses to corresponding electrodes.

Stimulation control module 62 also deactivates the regulated bidirectional current regulators of current regulator array 68 tied to inactive electrodes, i.e., electrodes that are not active as regulated electrodes in a given electrode configuration. Each regulated bidirectional current regulator of current regulator array 68 may include an internal enable switch controlled by stimulation control module 62 that disconnects regulated power source 64 from the current regulator or otherwise disables the current source when the corresponding electrode is not used as a regulated electrode to deliver stimulation.

In accordance with this disclosure, techniques are described for determining and presenting to a user an indication of energy consumption in an implantable medical device system, such as, for example, an electrical stimulator. For example, a programmer may provide an indication of energy consumption of an electrical stimulator for a given set of therapy parameters, such as electrode combination, electrode polarity, current or voltage amplitude, pulse rate, pulse width and/or duty cycle. The energy consumption for a selected set of therapy parameters, or a change in an individual therapy parameter, may be expressed in a variety of ways, including a energy efficiency rating that indicates relative energy efficiency on a given scale, absolute energy consumption or rate of energy consumption that indicates an amount of current, voltage, charge (coulombs), wattage consumed by the stimulator during delivery of therapy, and/or device longevity in terms of an amount of time remaining before a rechargeable battery that powers the device should be recharged, or the amount of time remaining before a non-rechargeable battery is depleted.

In one example, the indication of energy consumption may be expressed as an indication of battery longevity, given the rate at which energy will be consumed for a selected set of therapy parameters for a program, or sets of therapy parameters that may be associated with multiple programs in a group. In a stimulator, the longevity of a primary power source prior to depletion or the longevity of a rechargeable power source between recharges may be influenced by such factors as, for example, the voltage and/or current amplitude of stimulation pulses, pulse rate (i.e., frequency), pulse width, the number and type of electrodes activated, the impedance presented by those electrodes (e.g., by the electrodes and conductors that couple the electrodes to a stimulation pulse generator and by the impedance at the electrode-tissue interface), the number of programs active, the use of other features such as, for example, cycling on/off times of stimulation (this parameter indicates how long stimulation is on and how long it is off within a time frame), the age and charge level of the power source, and the energy consumption of the stimulation engine associated with these other inputs. In addition, the energy consumption of the stimulation engine may change over time as one or more of the parameters is adjusted by a patient using a programmer or by adaptive stimulation algorithms driven by a sensing mechanism within the device. As power sources in rechargeable devices continue to decrease in size, managing the parameters that may affect the longevity of the power source in an interactive manner may become more important. Accordingly, it is desirable to provide presentation of a user interface that permits the user to view an energy consumption estimate in conjunction with therapy parameters that may be selected by the user.

Figure 6A:
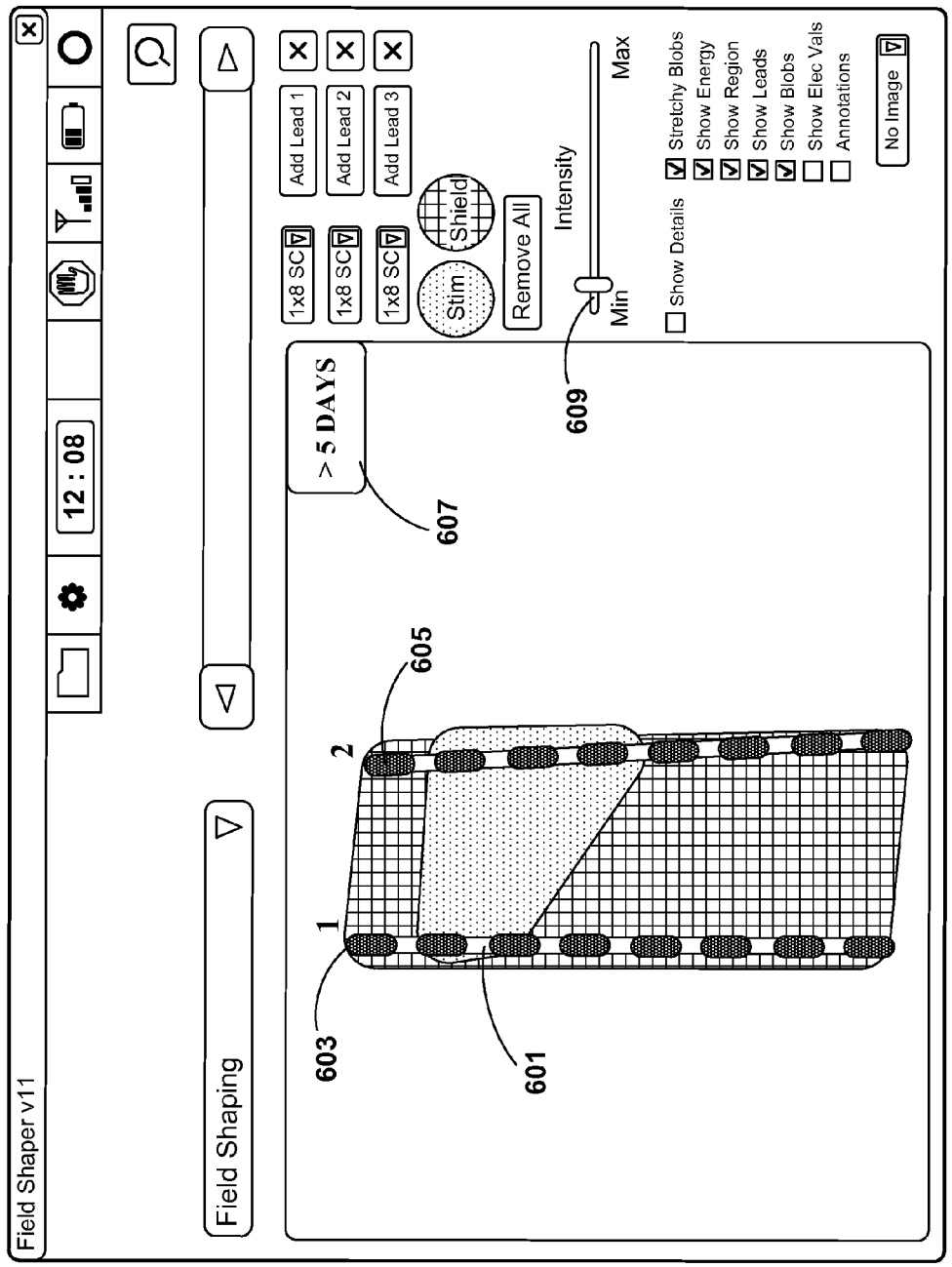
FIGS. 6A-6B illustrate a user interface of a programmer showing a power source charge indicator.

FIG. 6A illustrates a user interface of a programmer showing a power source charge indicator. A user may utilize a programmer with a user interface, such as, for example, the user interface of FIG. 6A to select parameters for a therapy delivered to a patient. Using the parameter information entered by the user with data about the stimulation engine's performance (e.g., actual or historical energy consumption data corresponding to therapy delivered using the parameters), which may be known, the programmer may determine a metric of time until the power source needs a recharge. The metric of time until the power source needs a recharge depends on an estimate of a current capacity of the power source, i.e., a total amount of power remaining in the power source, and an estimate of future drains on the power source.

An estimate of the current capacity of the power source may be based on one or more of the following: a real-time measurement corresponding to the current capacity of the power source, such as a voltage measurement, and/or an estimate or measurement of a previous current capacity of the power source combined with estimates and/or measurements of current consumed since the previous current capacity of the power source.

An estimate of current consumed may be based on one or more of: battery capacity measurements using a coulomb counter, battery capacity measurements using a capacity-by-voltage device, a software coulomb counter, or measurements using a charge-time measuring device. An estimate of future current drains on the power source may be based one or more of: a real-time measurements of current consumed for selected therapy programs and program groups, recorded measurements of current consumed for selected therapy programs, parameters or parameter changes, predictions based on therapy parameters, measured resistances between selected electrodes, electrode resistances (for current capacity), measured or stored stimulation generator efficiency predictions and estimates of battery self drainage. For example, for charge amplitude stimulation programs higher resistances provide greater drains on the power source.

The programmer may also use information regarding the current capacity of the power source and information about energy consumption as determined by the coulomb counter, for example, to determine the amount of time left until a recharge of the power source is needed, or until the power source is depleted in the case of a non-rechargeable battery. As an example, some techniques for measuring charge consumed, estimating a current capacity of a power source, estimating of future drains on the power source, and estimating remaining battery life are disclosed in U.S. Pat. No. 7,142,923 to North et al., titled, "IMPLANTABLE NEUROSTIMULATOR PROGRAMMING WITH BATTERY LONGEVITY INDICATION," the entire contents of which is incorporated by reference herein.

In addition, in cases where parameters are not constant over time (i.e., either adjusted by a patient or an algorithm), scheduled program therapy changes, the historical averages or trends of parameters changes may also be used by the programmer to increase the accuracy of the predicted time left until recharge. For example, the estimation of energy consumption may be based on a real-time measurement of energy consumption for the selected therapy parameters or a model that estimates energy consumption for the selected therapy parameters. The model may be calibrated based entirely on actual measurements taken following implantation of the IMD in the patient or actual measurements taken following implantation of the IMD in the patient (such as measurements taken by a coulomb counter, electrode/lead impedance measurements) as well as information stored in memory of the IMD or programmer that is the same for each of a series of substantially identical IMDs manufactured along a common assembly line (such as estimates of battery self-drainage, an estimates of energy consumption associated with a stimulation generator etc.). In summary, any suitable combination of historical information unique to the IMD, real-time measurements and/or information stored in memory that is the same for a series of substantially identical IMDs manufactured along a common assembly line may be used to determine an estimate of future energy consumption in order to determine a metric of time until the power source needs a recharge. In different examples, the metric indicated by the programmer may be expressed in unitless energy consumption units (e.g., a range representing relative values), or expressed in terms of time units such as, for example, days between recharge, days/hours until the next recharge, days/hours until complete depletion, or years of device life.

In the example of FIG. 6A, the user interface may show a stimulation therapy session using field shaping, where a user may define the stimulation zone 601 as the desired region to receive therapy from at least a portion of leads 603 and 605. As seen in the lower right portion of the screen, the user may select what to show on the display. In this example, one of the choices is "Show Energy," which may be associated with an energy indicator 607. In this example, the user had selected two leads, had drawn the blob 601 representing the zone where the stimulation therapy should be applied, and selected the desired intensity of the leads using the intensity selection button 609, which may be, as shown in this example, an on screen button that can be moved, e.g., a slider bar, within a range representing minimum to maximum intensity that can be applied within the stimulation zone.

The programmer may calculate separate energy consumption estimates for each stimulation pulse delivered via the electrodes associated with the stimulation zone. An energy consumption estimate for a selected set of stimulation parameters represents the new energy consumption for all the stimulation pulses for the selected set of stimulation therapy parameters. In some cases, the user may size, shape and reposition the stimulation zone, as well as adjust zone intensity. The amplitude values may be weighted based on relative contributions of the respective electrodes to the delivery of stimulation corresponding to the size, shape and/or intensity of the stimulation zone. Hence, each electrode associated with a stimulation zone, e.g., each electrode that resides within or overlaps a stimulation zone, may have a pulse amplitude that is determined as a function of the respective weight and the overall intensity selected for the zone. A variety of functions, including geometric functions, may be used to compute the weights based on the position of the electrode relative to the stimulation zone and relative to other electrodes in the zone.

In another example, the intensity may be expressed in numerical values and/or may be individually definable for each electrode within the leads 603 and 605. In either case, whether for discrete electrode programming or zone-based programming, the user interface may display the energy indicator 607 corresponding to the selected therapy parameters, for example, ">5 days" indicating that the power source will operate for more than 5 days before recharge may be needed. For example, the programmer may determine that, for a given set of therapy parameters, the rate at which energy that will be consumed will result in a particular longevity time for which the battery may be used at that rate before recharging is necessary. In an example, the color of the energy indicator 607 may also indicate a status or certain messages. In this example, the energy indicator 607 may be depicted in green, indicating that the amount of time of remaining energy may be sufficient for at least a threshold period of time, e.g., 5 days, and that the user need not yet worry about recharging. As time goes by, the energy level may get to a point where a user may need to be alerted that there is less than a threshold period of time remaining before the power source may require a recharge, e.g., 1 day, and the indicator may be displayed, for example, in red. Hence, different colors may be used to indicate different status levels of the battery longevity state. Additionally, or alternatively, other techniques may be used to indicate different status levels, such as blinking or flashing text, highlighted text, special graphical icons, audible alerts, tactile alerts and the like. These indications and their behavior may occur at fixed thresholds or at thresholds configured by a given user, for a given therapy, or customized to a specific patient's tolerances. It should be understood that while the longevity of the power source is discussed in units of days in this disclosure, that other units of time such as, for example, weeks, hours, minutes, etc., may be also used.

In accordance with techniques of this disclosure, the user interface as shown in FIG. 6A may allow the user to select one of several lead configurations. In the example shown in FIG. 6A, the selected configuration may allow the user to define therapy using field shaping, by manipulating the shape of the region where therapy may be delivered. Additionally, the user may select the number of leads used to deliver the therapy, and the number of electrodes in each lead. In this example, the user selected to use two leads with 8 electrodes each. As shown on the right side of the user interface, up to three leads may be added in this example. In other examples, more leads may be available. The user may also be able to use the user interface to manipulate the positions of the leads, select a stimulation (cathode) and/or shield (anode) status, and associate polarities for particular electrodes. Additionally, when using zone programming, as shown in this example, the user may be able to move, stretch, or shrink blobs representing the stimulation zones. In one example, the user may be able to use the field shaping mode with stimulation zones, or select a different mode such as, for example, programming individual electrodes.

Figure 6B:
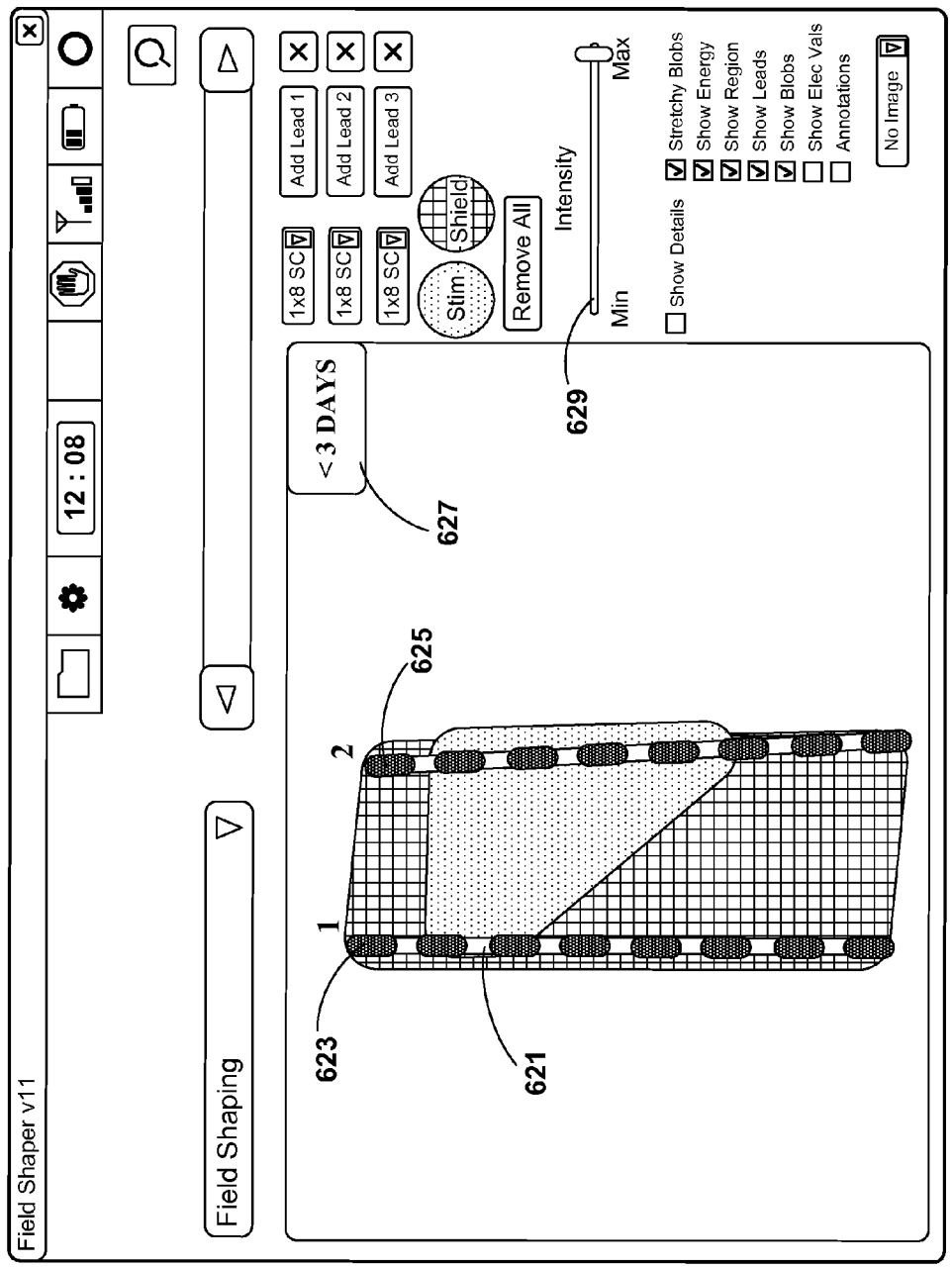

FIG. 6B illustrates a user interface of a programmer showing a power source charge indicator. In this example, the user may have modified the parameters of the desired therapy from the parameters illustrated in FIG. 6A. In particular, the user increased the area of the stimulation zone to a larger stimulation zone 621. Additionally, the user selected to increase the intensity of the stimulation within the stimulation zone 621 to the maximum intensity, as illustrated by the intensity selection mechanism 629. These changes in parameters may alter the time until recharge, and it may be expected that increasing the intensity applied and the area of the stimulation zone where the intensity is applied would shorten the time left before the power source may require a recharge. As expected, the amount of time until recharge decreased from over 5 days as shown by the energy indicator 607 of FIG. 6A, to less than three days as shown by the energy indicator 627 of FIG. 6B. In this example, the amount of time until recharge is needed is less than 3 days, which may require the attention of the user, either to alert the user regarding the energy consumption of the parameters selected such that the user may select a different set of more energy efficient parameters, or to ensure that the energy level is checked so as to ensure recharging the power source in a timely manner. In this example, the energy indicator 627 may be displayed in red, or with other indicators, to alert the user that there is relatively a short time left until recharge is needed or that energy consumption has been increased by the currently-selected parameters. As the user adjusts the parameters, the programmer may adjust the longevity indicator in real-time, which informs the user of the change to the time until recharge as a function of the adjusted parameter, and allows the user to make a choice of which parameters to apply. In an example, the user may be able to see in real-time the effect of different combinations of parameters on the time until recharge, and may therefore be able to determine the effect of different combinations on power source longevity.

Figure 7A:
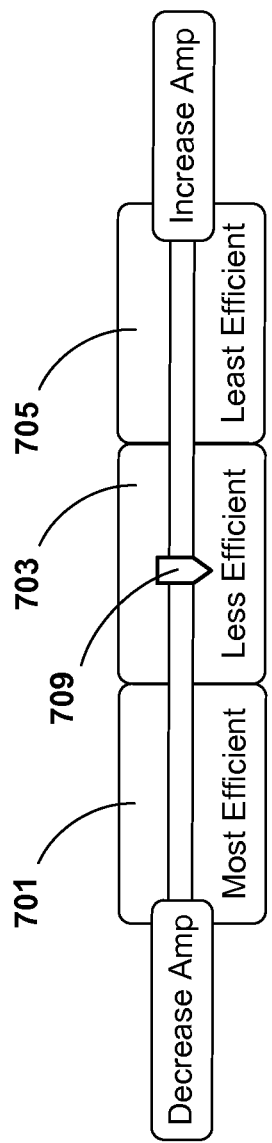
FIG. 7A illustrates a user interface of a programmer presenting example control media provided to a user for programming amplitude of stimulation therapy.

FIG. 7A illustrates an example control mechanism that may be provided to a user via a user interface of a programmer for programming amplitude of a stimulation. In this example, a control may be displayed to allow the user to select a parameter, such as, for example, the amplitude of stimulation within a therapy region. As an example, the control mechanism may be included in conjunction with the user interface shown in FIGS. 6A and 6B and may be presented in combination with an indication of an energy consumption estimate for selected stimulation parameters including the stimulation parameters selected with the control mechanism of FIG. 7A.

The control may include a slideable indicator 709. For example, the position of slideable indicator 709 may be adjusted using a stylus in the case of a touch-screen or using buttons of the programmer. The selection mechanism provided to the user may be color coded and/or text coded so that a user may know as he/she selects the amplitude, what the effect will be on the energy consumption. As indicated in the example of FIG. 7A, the smaller the (voltage or current) amplitude is, the less the energy consumption will be for the system, and the higher the amplitude is, the less efficient the energy consumption will be. This may also be color coded in the example of FIG. 7A, where the range is superimposed on three blocks ranging from Most Efficient 701 to Least Efficient 705, corresponding to low amplitude to high amplitude, respectively. A middle block, Less Efficient 703, may be inserted between the two extremes. In other examples, more blocks may be used to provide more defined increments of the energy consumption within the range. In other examples, the energy consumption of the system may be represented quantitatively within the range with several different gradations and associated energy consumption values. In yet another example, the range may be continuous with no distinct blocks, and color coded along a spectrum to represent the change in the level of energy consumption. In each case, a block, gradation, or point within the range represents the trade-off between increased and decreased stimulation amplitude value, or some other parameter value such as pulse width or pulse rate, and the resulting energy consumption resulting from selection of that parameter value.

Figure 7B:
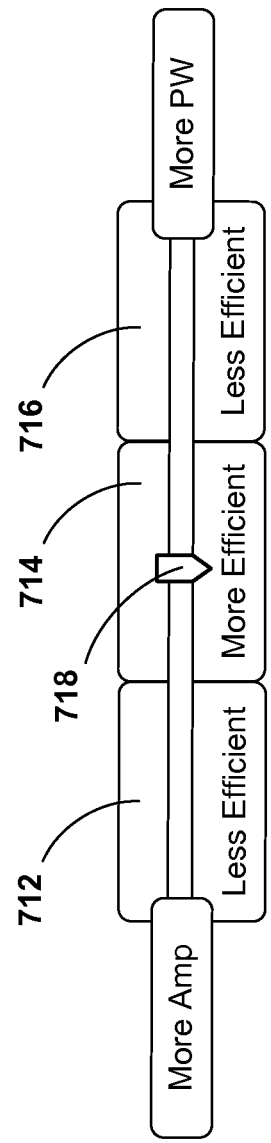
FIG. 7B illustrates a user interface of a programmer presenting example control media provided to a user for programming amplitude and pulse width of stimulation therapy relative to one another.

FIG. 7B illustrates an example control mechanism provided to a user for programming amplitude and pulse width of stimulation therapy program or program group relative to one another. As an example, the control mechanism may be included in conjunction with the user interface shown in FIGS. 6A and 6B and may be presented in combination with an indication of an energy consumption estimate for selected stimulation parameters including the stimulation parameters selected with the control mechanism of FIG. 7B. In this example, a control may be displayed to allow the user to effectively select two parameters relative to each other by positioning slideable indicator 718. In this example, of FIG. 7B, the two parameters represent an energy consumption tradeoff against one another.

The position of slideable indicator 718 may be adjusted using a stylus in the case of a touch-screen or using buttons of the programmer. In the example of FIG. 7B, the user may select more amplitude versus more pulse width. The range in this example is effectively a combination of two ranges, where on one end the maximum amplitude with the minimum pulse width may provide less efficient stimulation in terms of the energy consumed by the system, as may the values on the other end, the minimum amplitude combined with the maximum pulse width, and where somewhere in the middle of the range, where there is a trade off between pulse width and amplitude, a more efficient energy consumption may be achieved. This control mechanism may be color coded as discussed with respect to the selection mechanism of FIG. 7A, where the range is superimposed on three blocks ranging from Most Efficient 701 to Least Efficient 705, corresponding to low amplitude to high amplitude, respectively. A middle block, Less Efficient 709 may be inserted between the two extremes. In the example of FIG. 7B, the range may be superimposed on three blocks that go from Less Efficient 712 to More Efficient 714, and again to Less Efficient 716, corresponding to a trade off range between pulse width and amplitude. In other examples, more blocks may be used to provide more defined increments of the efficiency within the range. In other examples, the energy consumption estimate of the system may be represented quantitatively within the range, for example, in terms of the time until recharge, so instead of the "Most Efficient" block, there may be a block ">5 days" and instead of the "Least Efficient" block, there may be a block "<3 days," etc. In yet another example, the range may be continuous with no distinct blocks, and color coded to represent the change in the level of efficiency.

In the examples of FIGS. 7A and 7B, the slider between the two values or two extremes may have quantitative values, instead of relative values ranging from Most Efficient to Least Efficient. For example, the slider may have expected time until recharge values ranging from ">7 days" to ">5 days" to "<3 days" or unitless values ranging, for example, from 0 to 100. The slider position represents parameter values that correspond to the expected time until recharge. When a user adjusts the slider position, the selected stimulation therapy parameters are likewise adjusted.

Figure 8:
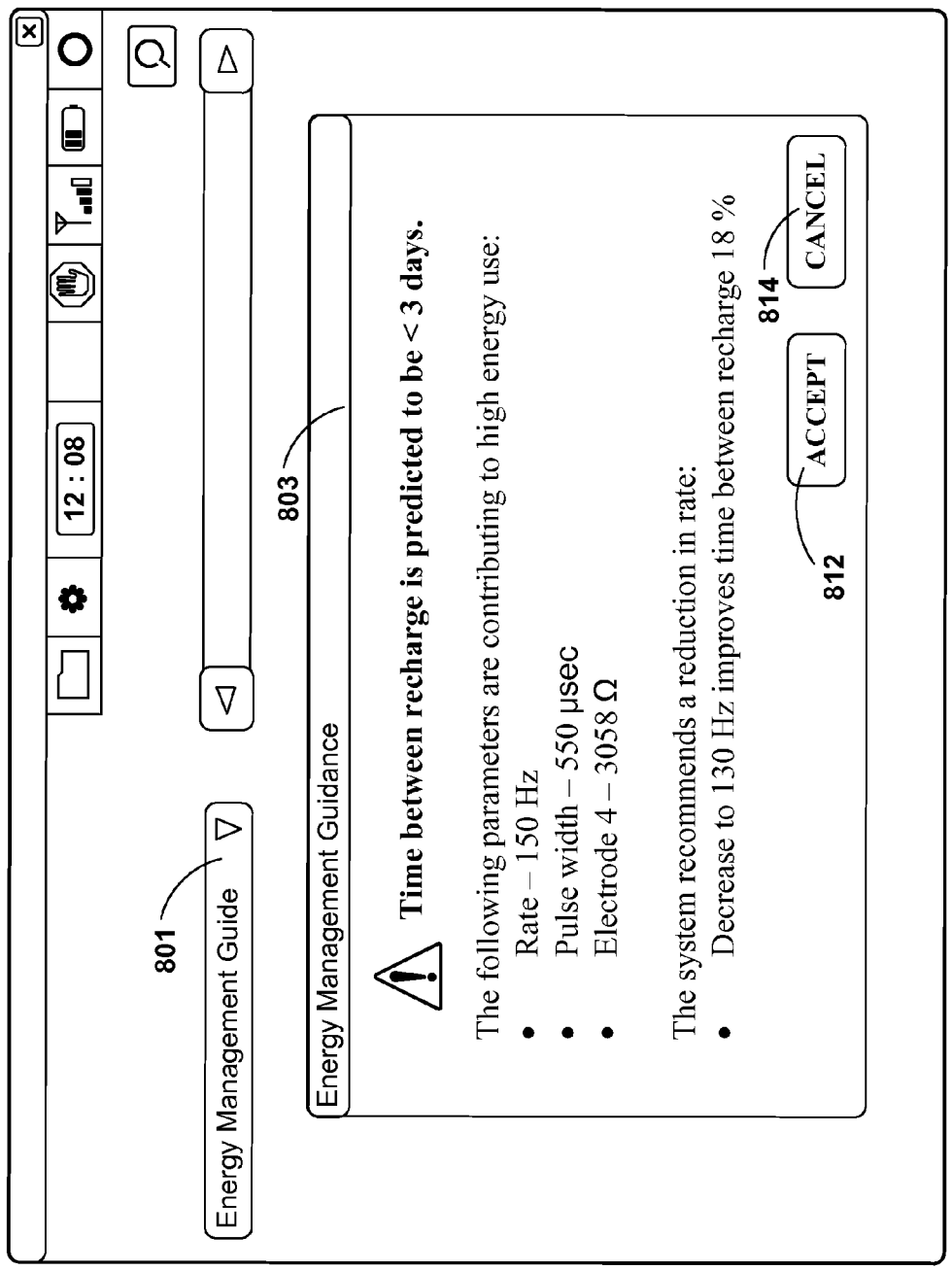
FIG. 8 illustrates a user interface of a programmer providing feedback for optimizing energy consumption during programming.

FIG. 8 illustrates a user interface of a programmer providing feedback for optimizing energy consumption during programming. During programming, the user may be provided with a choice to select a mode of operation where the programmer may provide suggestions of, for example, manipulations and parameter programming options that may optimize energy consumption. Upon selecting the option to receive suggestions, e.g., by navigating to the "energy management guide" of drop-down menu 801 the content of the suggestion may be displayed as a pop-up 803 within the display of the user interface, or it may be part of another context sensitive content. The programmer may be capable of determining which of the parameters used in programming stimulation therapy causes the most energy consumption and, conversely, which parameters may have the largest impact in increasing or reducing energy consumption. This determination may be based on known or previously measured efficiencies or inefficiencies of a stimulation engine, such as, for example, energy consumption calculations made during a previous session or during a previous therapy period. Such data may be provided in advance to the system or may be, for example, measured by the system during a session specifically dedicated to making energy consumption calculations. The programmer may also provide suggestions of how to change a parameter so as to optimize energy consumption.

Optimizing energy consumption refers to increase efficacy of a stimulation therapy relative to the energy consumption of the therapy. As an example, minor changes to rate are less likely to cause a gross difference in paresthesia than minor changes to amplitude. For this reason, a therapy adjustment suggestion may suggest a reduction in rate rather than a reduction in amplitude of stimulation pulses. In this manner, suggestions to change stimulation therapy parameters may focus on parameters that are relatively less likely to be therapeutically sensitive to minor changes. Further, energy consumed for a particular set of selected stimulation therapy parameters, e.g., one stimulation therapy program in a stimulation therapy program group, may be categorized as being within a "normal" energy consumption range or "high" energy consumption range. If a particular set of selected stimulation therapy parameters is in the "high" energy consumption range, a suggestion for reducing energy consumption may focus on the selected stimulation therapy parameters within the "high" energy consumption range.

The guidance provided by the programmer may be qualitative, e.g., "the system is running at a very high rate. Reduce it to improve longevity." The qualitative guidance may make general statements regarding one or multiple parameters. The guidance may also be quantitative, specifying an exact amount by which to reduce a certain parameter, e.g., "A reduction of 20 Hz for rate will increase longevity by 13%." The quantitative guidance may make more specific statements regarding one or more parameters. In one example, the guidance may recommend using a different set of electrodes and/or electrodes delivering stimulations at different values. In the example of FIG. 8, the guidance pop-up may be made to look like a warning message, alerting the user that a selected group of parameters may cause the time to recharge to drop below a threshold that induces the pop-up to appear, for example, "<3 days."

The pop-up may then list the parameters that contribute to the inefficiency in energy, and may then make a recommendation regarding one of the parameters or all of them. The guidance pop-up may also provide the user with the option to "Accept" the recommendation provided by the programmer by selecting clickable button 812 or "Cancel" the recommendation by selecting clickable button 814. In another example, making a selection as to "Accept" or "Cancel" may prompt the user with a similar guidance pop-up, with a suggestion to alter another one of the parameters causing the energy consumption level to be high. For example, in FIG. 8, the guidance pop-up recommends to the user to decrease the pulse rate from 150 Hz to 130 Hz. If the user accepts, the programmer may decrease the rate. Upon accepting the recommendation, the programmer may minimize the pop-up, or may go on to recommend other ways to improve energy consumption by, for example, recommending an alternative pulse width, then an alternative resistance value for an electrode causing high energy consumption as shown in this example. In some examples, the pop-up may disappear once a user selects to accept or cancel the recommendation, but the pop-up may appear again if the energy consumption increases again above a certain level or if the time until recharge drops below a certain level and another recommendation may be made accordingly. As examples, the certain levels may be consistent predetermined levels or dependent on the remaining capacity of the battery as set by a user. It may be possible to select, for example, by a check box or other means, among multiple provided options prior to accepting the recommendation, which may result in all selected options being implemented by the system.

Figure 9:
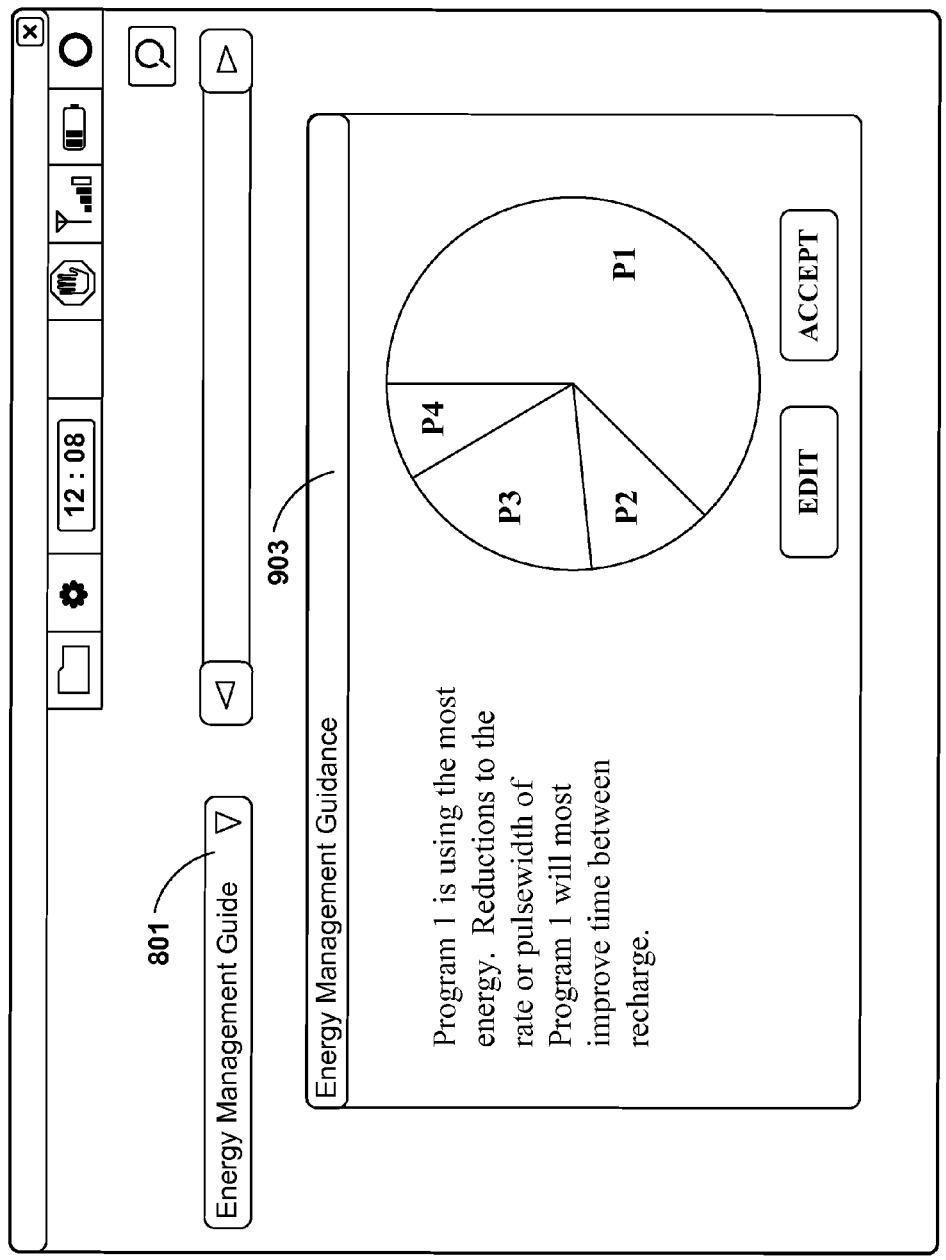
FIG. 9 illustrates a user interface of a programmer providing feedback for optimizing energy consumption during programming of multiple programs.

FIG. 9 illustrates a user interface of a programmer providing feedback for optimizing energy consumption during programming of multiple programs. The user may wish to program several programs at once, to provide stimulation therapy to multiple regions. In a situation where multiple programs may be activated together, the actual time until recharge or longevity of the power source may be determined by the sum of all active therapy programs. In some examples, there may be some interaction between the programs or settings at a system level, i.e., global parameters, which may further impact the power source longevity. The system may provide the user with the ability to see the contribution of each program on the overall energy consumption, and therefore, the contribution of each program on the longevity of the power source and the efficiency of the system.

During programming, the user may be provided with a choice to select a mode of operation where the programmer may provide suggestions of, for example, manipulations and parameter programming options that may optimize energy consumption. Upon selecting the option to receive suggestions, e.g., by navigating to the "energy management guide" of drop-down menu 801 the content of the suggestion may be displayed as a pop-up 903 within the display of the user interface, or it may be part of another context sensitive content. For example, pop-up 903 may be displayed in series with multiple suggestions such as the suggestion provided by pop-up 803 (FIG. 8). In such an example, a different suggestion pop-up may be presented to a user automatically following the acceptance or cancelation of a previous suggestion. In this manner, navigation to the "energy management guide" of drop-down menu 801 may begin a process in which any number of suggestions is presented to the user.

In the example of FIG. 9, there may be four programs active at once, programs P1, P2, P3, and P4. The user interface may provide the user with a graphic, such as, for example, a pie chart, or any other type of graphic to indicate the proportional effect on the overall energy consumption of the system contributed by each program. In this example, program P1 may be responsible for using the most energy among the four programs. The user interface also present an indication of the contribution of power consumption of each program in other forms, for example, in the form of a numerical percentage value, a histogram, or the like. The user interface may also display text along with the graphical representation alerting the user as to which program is using the most energy, and a recommendation to improve the system's power source longevity. In this example, the user interface recommends that reducing the rate or pulse width of program 1, the one responsible for the most energy consumption, may improve the longevity of the power source of the system. In this example, a coulomb counter may be utilized in determining the contribution of each program. Each program may be applied for a short period, e.g., a few seconds, to get pulses that may be used to determine the contribution to the energy consumption. In another example, each program may be temporarily inhibited by the system and the difference in energy used by the remaining programs versus a baseline measurement may be used to determine the contribution of the inhibited program.

In this example, it may be less disruptive to the overall therapy when one program is inhibited, rather than turning each program on in turn independently.

In an example, a user may adjust a global parameter that affects all programs or a program parameter that is associated with one or more programs, and the user interface may adjust accordingly information regarding the effect of each program on the overall energy consumption of the system. Examples of adjusting a global parameter include reducing stimulation current amplitude for all programs, reducing stimulation voltage amplitude for all programs, reducing stimulation pulse rate for all programs and reducing stimulation duty cycle. Such global reductions may be on a discrete (e.g., 10 Hz) or percent basis.

For the example of FIG. 9, as a parameter is adjusted by the user, the pie chart may be adjusted accordingly in real-time, if for example, the parameter change alters the percentage contribution of any of the programs on the overall energy consumption. Additionally, the feedback text, as shown on the left side of the display of the example of FIG. 9, may be also updated accordingly in real-time.

It should be appreciated that the above systems and ways of improving the longevity of a system's energy may be used alone or in combination with one another. It should also be understood that the above example of parameters and ranges are exemplary, and that a system may use indications for any one or more of a number of parameters that may be programmed by a user in a stimulation therapy system.

Figure 10:
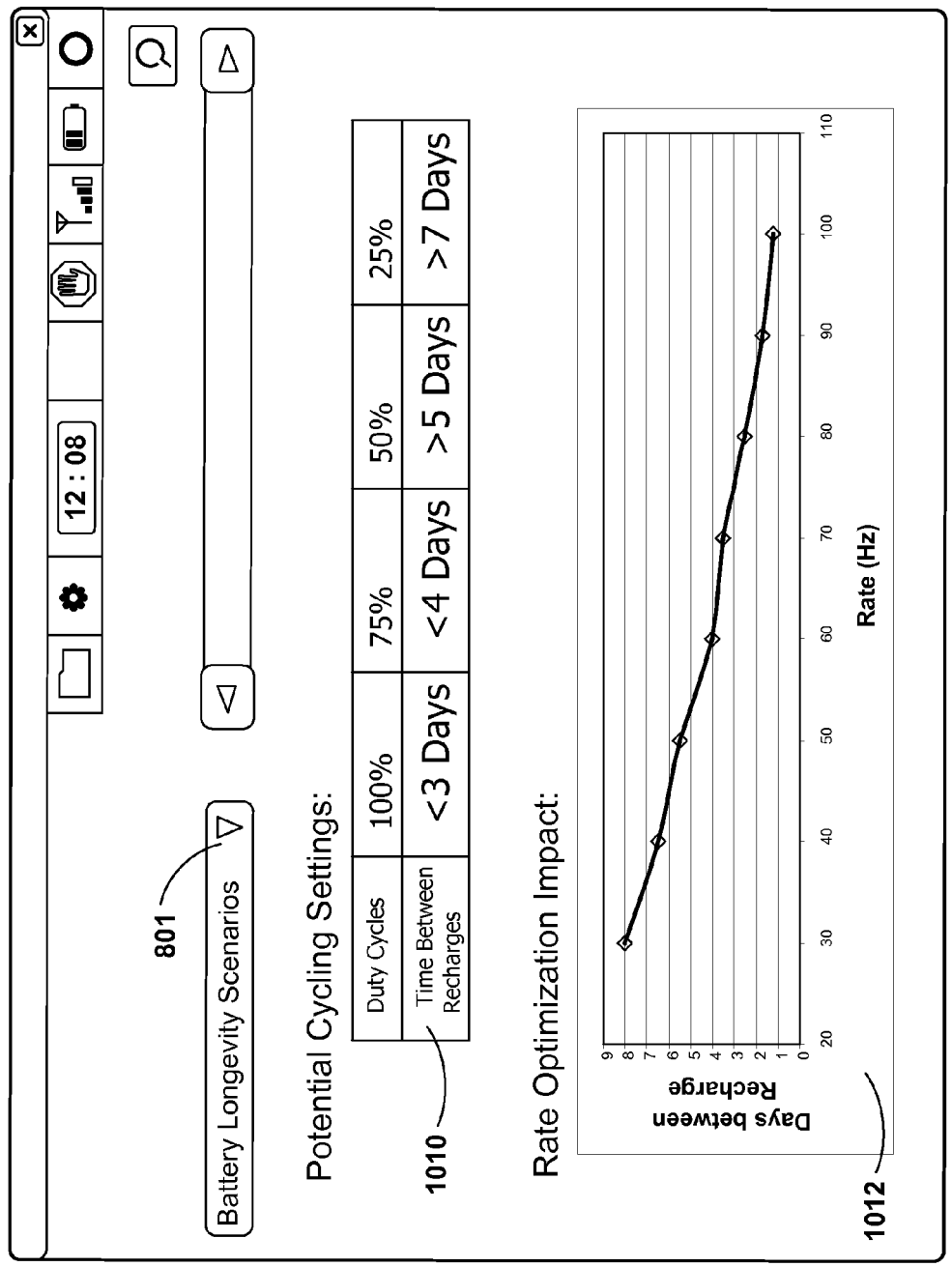
FIG. 10 illustrates a user interface of a programmer providing predicted longevity values and corresponding scenarios.

FIG. 10 illustrates a user interface of a programmer providing predicted longevity values and corresponding scenarios, for a given program or group of programs, with different duty cycles. In an example, a user may navigate to the user interface of FIG. 10 by selecting the "battery longevity scenarios" within drop-down menu 801. A duty cycle may define the time for which a given program, or all of the programs in a group, is turned ON, versus a time that they are turned OFF. In one example, the system may provide a user with different options to reduce energy consumption in a system, and the effect of each option in terms of the longevity, at a program level and/or at the system level. In this example, the top portion of the user interface display shows a table 1010 of predicted longevity values versus the duty cycle of the stimulation delivered according to a selected program or group of programs. For example, a 100% duty cycle may provide the most therapy, but the longevity of the system is reduced greatly, to less than 3 days between recharges of the power source in this example, whereas, a 25% duty cycle may provide less therapy, but may have a longer time between recharges of more than 7 days in this example. Table 1010 in FIG. 10 shows an example of providing a few options, e.g., four (100, 75, 50 and 25 percent). In another example, the options may be displayed in a more continuous fashion, such as, for example, using a plot 1012 as shown in the bottom part of the user interface display of FIG. 10. Plot 1012 illustrates the effect of increasing or decreasing the pulse rate on the number of days between recharges. In this example, the minimum rate is 30 Hz, corresponding to a maximum of 8 days or more than 7 days between recharges, whereas, the maximum rate of 100 Hz, corresponds to a minimum time between recharges of 1 day. In other examples, the plot may depict a minimum recharge time of less than 1 day. This relationship is represented with a plot that shows a continuous relationship instead of the table showing fewer options. This predicted longevity indication may be provided for each program separately or for the entire system as a whole delivering multiple programs in a selected group of programs, where for example, the user may be presented with options that affect one program's parameters or a global parameter, with the effect of optimizing or reducing the energy consumption of the entire system. In this example, the displayed information may be informational, where the user sees a plot or chart of changes and the corresponding effects, or interactive, where the user may be able to select one of the changes to get the corresponding effect.

In another example, historical therapy data such as, for example, the amount of time therapy is actually used (versus assuming therapy is used 24 hours a day or another "generic" assumption"), may be used to provide a more detailed and accurate prediction of longevity of the power source of a system. The historical data may be tracked by the stimulator and stored in the memory of the stimulator and retrieved by a user of the programmer during a programming session. The predictions may be further tailored by tracking historical usage of actual parameters versus clinician parameter settings, in situations where the patient may have control over at least a portion of the parameters. This may be further used to determine longevity versus effectiveness of therapy, if it is assumed that the parameter settings by the patient correspond to a more effective therapy, as the patient may alter the parameters to accommodate his/her pain level, for example. In one example, where sensor devices may be used to sense one or more patient parameters or conditions used to control therapy delivery, information about the patient parameters and/or conditions may be tracked to provide more detailed prediction of the power source longevity metric. For example, when sensors are used to determine patient activity and/or posture, so that therapy may be delivered based on these sensed conditions, actual times in postures or activities and their associated average parameter settings may be used to provide more detailed prediction of the longevity metric. Other types of patient parameters may be tracked in a similar manner and used to predict the longevity metric.

In accordance with the techniques described in this disclosure, the stimulation device may use, for example, a coulomb counter to directly measure the charge that is delivered from the power source to support delivery of therapy for a given set of therapy parameters, which may be associated with a single program or a group of programs. For example, the coulomb counter may determine the amount of charge delivered over a period of time, as an indication of energy consumption. The stimulator or the programmer then may use the determined amount of charge to determine the energy consumption estimate of the device, e.g., in terms of rate or energy consumption in watts or milliamp-hours, or estimated remaining before recharge is necessary in a rechargeable battery or before battery depletion occurs in a non-rechargeable battery, which may be expressed as device longevity (e.g., >5 days, <3 days, etc. When a user updates the parameters, the stimulator may again measure charge delivered to support the stimulation pulses associated with the updated parameters, and the time to recharge period (i.e., time between power source recharges) may be recalculated and displayed to the user. The characterization of the settings and the predicted time until recharge and/or longevity based on a set of parameters may be measured by a calculation based on the associated pulses or based on a programmed formula and/or historical data.

Figure 11:
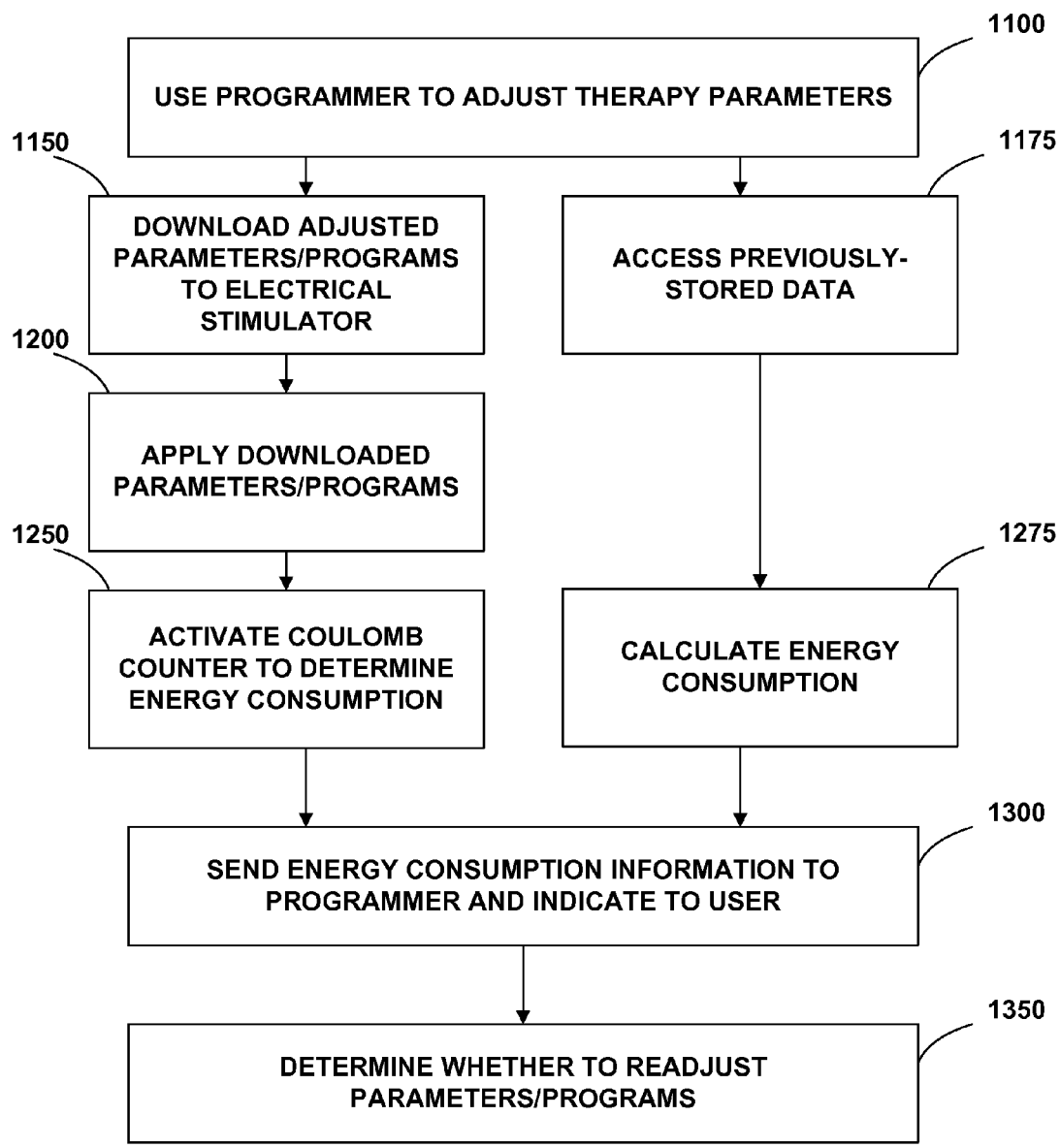
FIG. 11 illustrates an exemplary flow diagram of energy management in an electrical stimulator system, in accordance with this disclosure.

FIG. 11 illustrates an exemplary flow diagram of energy management in an electrical stimulator system, in accordance with this disclosure. A user may use a programmer, such as, for example, programmer 20 or 40 of FIGS. 1 and 2, respectively, to program stimulation therapy by selecting parameters (1100) defining the therapy. The programming may be direct, i.e., selecting parameters for electrodes individually, or zone-based, i.e., by defining characteristics or parameters of a zone where therapy is to be applied. The parameters may define a new program or set of programs or may modify an existing program or group of programs. The user may then use the programmer to download the adjusted program, adjusted group of programs, or adjusted parameters for programs or group of programs to the electrical stimulator (1150). The electrical stimulator may then apply the downloaded therapy program or programs (1200) and activate a coulomb counter associated with the electrical stimulator to determine energy consumption and/or time until recharge associated with the adjusted therapy program or programs (1250). In an example, the energy consumption and/or the time until recharge may be determined on parameter-by-parameter basis, where each parameter adjustment may be applied separately, and the energy consumption may be determined for each parameter adjustment. In another example, the energy consumption and/or the time until recharge may be determined for all parameter adjustments applied at once, or for the entire group of programs. In another example, each program in a group of programs may be applied separately to determine the energy consumption and/or the time until recharge associated with each program. In one example, the coulomb counter may measure the amount of current output by the power source to determine the amount of energy consumption of the power source for an active program. In another example, the coulomb counter may measure the amount of current output by the power source relative to the amount of charge remaining in the power source to determine the amount of time until recharge.

Once the energy consumption and/or the time until recharge are determined, that information may be sent back to the programmer (1300). The programmer may then indicate to the user the energy consumption for the selected/adjusted parameters/program(s) via the user interface of the programmer (1300). Based on the indicated energy consumption values, the user may decide whether or not to readjust the parameters/program(s), and how to readjust them (1350).

Alternatively, after adjusting the parameters/program(s) (1100), the programmer may rely on previously-stored or previously-acquired information (1175) to calculate the energy consumption (1275). Some previously-stored or previously-acquired information may be, for example, actual historical usage (number of hours per day during which stimulation is activated), actual historical parameter values (i.e., parameters are typically 15% lower on average than the value set in clinic due to patient adjustments or sensor algorithm adaptation), actual recharge performance, which may account for a reduction in battery capacity over time, electrode/lead impedance and other electrode-/lead-related settings, power source discharge profile, measured current at a given pulse width, rate of stimulation, amplitude, cycling settings, patient usage data, sensor data, data relating to power source behavior, etc. In one example, the programmer may rely on a combination of previously-stored or previously-acquired information and actual information measured based on actual delivery of the therapy by the stimulator to determine the energy consumption of the stimulator.

In an example, the energy consumption of programs may be measured and determined by a coulomb counter in the electrical stimulator. When determining the energy consumption of a group of programs, the stimulator may determine the energy consumption of each program on its own by applying the therapy of the program and measuring the energy consumption for that program, then applying the next program and measuring the energy consumption, and so forth. The stimulator may send the energy consumption information for each program to the programmer to display to the user. The programmer may then display for the user information regarding energy consumption for each program and/or for the group of programs combined. When determining the energy consumption for each program, the stimulator may deliver the stimulation and measure the energy consumption, or may use historical data of previously-stored or previously-acquired information to calculate the energy consumption, or a combination of the two. In another example, the coulomb counter may make the necessary measurements for the calculation of the energy consumption, and may send the measurements to the programmer, for the programmer to calculate energy consumption and time until recharge.

More specifically, energy consumption estimates may be based on projected manual adjustments to stimulation therapy by the patient. The projected manual adjustments may be based on a historical record of past manual adjustments to stimulation therapy by the patient. The projected manual adjustments may be specific for a selected set of therapy parameters. Because manual adjustments to stimulation therapy by the patient may increase energy consumption, the energy consumption estimate for a stimulation therapy program may not directly correspond to the energy usage of the therapy parameters in the stimulation therapy program. For example, a stimulation therapy program which is historically associated with manual patient adjustments increasing the current or voltage amplitude of the program would be associated with a higher energy consumption estimate. In addition, energy consumption estimates may be based on projected patient postures and automatic and/or manual therapy parameter adjustments associated with the projected patient postures. The projected patient postures may be based on a historical record of past patient postures.

Techniques of this disclosure may provide all measurements and feedback to a user of the programmer regarding energy consumption in real-time during the programming of parameters. In doing so, the user may receive real-time predictions/projections of energy consumption for prospective therapy parameters from which the user may select for application to the electrical stimulator. The user may be able to select parameters based on a desired energy consumption level.

In an example, the coulomb counter may calculate the energy consumption associated with delivery of stimulation according to a set of parameters. In one example, the coulomb counter may operate by averaging the energy leaving the battery over a period of time or a fixed number of pulses. For high stimulation rates, the period of time may be 2-4 seconds, and for low rate stimulations, the time period used by the coulomb counter may be extended (e.g., 10 seconds) or averaging may continue until enough pulses are included to deliver a desired accuracy. In an example where the device is not delivering continuously, the measurement performed by the coulomb counter may be synchronized to the beginning of a sequence of pulses or the measurement period extended to fully incorporate multiple cycles of pulses. If only the sequence of pulses is measured, the system may mathematically adjust for any periods of time in which the system is not delivering pulses (i.e., cycling off periods). In an example, other adjustments may be made to the measured energy value, such as, for example, scaling up or down based on likely or historically-measured variations in one or more parameters, as may be made by a patient programmer or an adaptive algorithm. This may include, for example, averaging out typical or historical periods where one or more programs are disabled by the patient or another automatic feature. The value measured by the coulomb counter may also be derated for future inefficiencies, such as, for example, a lower efficiency due to a decreased battery voltage or higher battery impedance that may occur over the course of a discharge cycle.

In one example, the coulomb counter may be connected to the power source, and may be able to determine the amount of current drawn out of it or the amount of current sent to it, thereby being able to determine the amount of energy consumed by a system using the power source. A power source to which the coulomb counter is connected may be rated with a certain power rating, in Amp-Hours, which may be measured. The coulomb counter may then be able to determine the amount of current that a certain stimulation or setting may cause to be drained from the power source. Using the power rating and the amount of current used by a certain setting, the time it takes to deplete the power source may be determined by simply dividing the current used by the power rating. For example, if we know we have "X" Amp-Hours left in a battery (power source) and the coulomb counter measures Y Amps drained out of the power source for a specific therapy setting, then it will take X/Y hours to deplete the power source.

In an example, the system may utilize a combination of techniques for predicting time between recharges of the power source to provide the user with interactive feedback, so that the desired and most appropriate setting may be selected. In an example, the programmer may determine the time until recharge based on an assumption of a full battery at the time the parameters are updated, or the stimulation device may measure the current level of the power source to provide a more accurate indication of the time until recharge. In determining the time until recharge and providing the user with recommendations and predicted values, an important criterion may be to have minimal therapeutic effects. For example, a change that may extend the power source time until recharge by one day may have less therapeutic effects than a change that extends the time until recharge by five days. In one example, the expected therapeutic impact may be indicated to the user for each recommended option to reduce the energy consumption.

In examples where the system may provide multiple options to reduce energy consumption, the user may be provided with check boxes to select multiple recommendations. When multiple recommendations are selected, the user may be provided with a corresponding expected time until recharge and therapeutic impact, i.e., an indication of the tradeoff between the benefit of a selection and the impact on the therapy delivered to the patient. In one example, the recommendations may not be applicable at the same time. In such an example, the recommendations may be grouped based on which may be applicable together, or upon selecting one recommendation, those that are not applicable may become grayed out or may be taken off the display.

In yet another example, the user may be able to preview the changes with the patient before confirming, by making selections of parameters or recommendations of parameter changes and applying the corresponding therapy to the patient to confirm whether the therapy level is still acceptable and effective. In an example, the patient may be capable of making changes to certain parameter using the patient's programmer, while away from a clinic. The parameters that the patient may change may be limited, as determined by the system.

Additionally, while aspects of this disclosure are described in the context of a stimulator as an implantable medical device, techniques described herein may be utilized in other types of medical devices which may be implantable. For example, techniques of the disclosure may be utilized with any type of a neurostimulator, or implantable fluid pumps where an image may show catheter configuration, and where therapy is delivered by pumping fluid such as blood, insulin, pain relief agents, or other medicine to the targeted therapy region. For example, in an implantable fluid device, the energy efficiency and time until recharge may be determined based on the energy consumed by a fluid pump for different rates of fluid delivery, duty cycle, volume of fluid delivered, etc. In another example, techniques of this disclosure may be employed in systems that include external stimulation devices, such as, for example, external stimulation devices such as those used for "trialing" procedures or for transcutaneous electrical nerve stimulation (TENs).

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various embodiments of the invention have been described. These and other embodiments are within the scope of the following claims.

The invention claimed is:

1. A programmer for an implantable medical device comprising:
   a user interface that receives user input corresponding to selected stimulation therapy parameters for delivering stimulation therapy to a patient with the implantable medical device; and
   a processor that:
   determines an energy consumption estimate of a power source based on the selected stimulation therapy parameters;
   controls the user interface to present the determined energy consumption estimate of the power source;
   determines that the energy consumption estimate is above a certain level,
   determines, in response to the determination that the energy consumption estimate is above the certain level, a respective value of a stimulation therapy parameter of the selected stimulation therapy parameters that causes a greatest amount of energy consumption of the selected stimulation parameters;

determines one or more programming options for altering the respective value of the stimulation therapy parameter to reduce the energy consumption estimate of the power source based on the selected stimulation therapy parameters, controls the user interface to present a recommendation of more than one of the one or more determined programming options to reduce the energy consumption estimate to the user with an indication that user selection of one or more of the recommended programming options would alter the respective value of the stimulation therapy parameter to reduce energy consumption of the implantable medical device, and receives user input, via the user interface, selecting one or more of the recommended programming options to reduce the energy consumption estimate presented via the user interface.

2. The programmer of claim 1, wherein the processor determines the one or more programming options for altering the respective value of the stimulation therapy parameter to reduce the energy consumption estimate in part by evaluating a proportional effect on the energy consumption estimate contributed by each program of a plurality of programs in a program group, and wherein each program of the plurality of programs in the program group defines a respective value for each the stimulation therapy parameters.

3. The programmer of claim 2, wherein the recommended programming options include an option to alter the respective value of the stimulation therapy parameter for the program of the program group that contributes the greatest proportion of the energy consumption estimate.

4. The programmer of claim 2, wherein the processor controls the user interface to present a representation of the proportional effect on the energy consumption estimate contributed by each program of the plurality of programs in the program group.

5. The programmer of claim 1, wherein the certain level represents a predetermined consistent level of energy consumption.

6. The programmer of claim 1, wherein the energy consumption estimate rises above the certain level when an estimated time until a recharge is required drops below a predetermined period of time.

7. The programmer of claim 1, wherein the user interface presents at least one of the recommended programming options using a slideable indicator that is moveable via user input to alter a recommended value of the respective value of the stimulation therapy parameter.

8. The programmer of claim 1, wherein the user interface presents at least one of the recommended programming options using a pop-up.

9. The programmer of claim 1, wherein the user interface presents the indication that user selection of one or more of the recommended programming options would alter the selected stimulation therapy parameters to reduce energy consumption of the implantable medical device using a color coded selection mechanism.

10. The programmer of claim 1, wherein the processor is configured to determine one or more modifications to the one or more programming options that reduce the energy consumption estimate while limiting any expected reduction in efficacy.

11. The programmer of claim 1, wherein the processor estimates a future drain on the power source, based on an association between the selected stimulation therapy parameters and historical usage of actual therapy parameters due to manual patient therapy parameter adjustments, to determine the energy consumption estimate.

12. The programmer of claim 1, wherein the processor estimates a future drain on the power source using a record of patient postures and therapy parameters associated with the patient postures to determine the energy consumption estimate.

13. The programmer of claim 1, wherein the one or more recommended programming options are selected from a group consisting of:
reducing stimulation current amplitude;
reducing stimulation voltage amplitude;
reducing stimulation pulse rate;
reducing stimulation duty cycle;
altering stimulation pulse width;
altering a number of activated leads or electrodes;
altering an electrode combination;
altering electrode polarity;
altering a number of active programs in a program group; and
altering a program selected for a slot of a program group.

14. The programmer of claim 1, further comprising a telemetry module that facilitates bi-directional communication between the programmer and the implantable medical device,
wherein the programmer receives the energy consumption estimate from the implantable medical device via the telemetry module.

15. A method comprising:
receiving, with a user interface of a programmer for an implantable medical device, user input corresponding to selected stimulation therapy parameters for delivering stimulation therapy to a patient with the implantable medical device;
determining an energy consumption estimate of a power source based on the selected stimulation therapy parameters;
presenting, with the user interface, the energy consumption estimate of the power source based on the selected stimulation therapy parameters;
determining, with a processor of the programmer, that the energy consumption estimate is above a certain level;
determining, in response to determining that the energy consumption estimate is above the certain level, a respective value of a stimulation therapy parameter of the selected stimulation therapy parameters that causes a greatest amount of energy consumption of the selected stimulation parameters;
determining one or more programming options for altering the respective value of the stimulation therapy parameter to reduce the energy consumption estimate of the power source based on the selected stimulation therapy parameters,
presenting, with the user interface, a recommendation of more than one of the one or more determined programming options to reduce the energy consumption estimate to the user with an indication that user selection of one or more of the recommended programming options would alter the respective value of the stimulation therapy parameter to reduce energy consumption of the implantable medical device; and
receiving user input, with the user interface, selecting one or more of the recommended programming options to reduce the energy consumption estimate presented via the user interface.

16. The method of claim 15, wherein determining one or more programming options for altering the respective value of the stimulation therapy parameter to reduce the energy consumption estimate of the power source based on the selected stimulation therapy parameters comprises evaluating a proportional effect on the energy consumption estimate contributed by each program of a plurality of programs in a program group, and wherein each program of the plurality of programs in the program group defines a respective value for each the stimulation therapy parameters.

17. The method of claim 16, wherein the recommended programming options include an option to alter the respective value of the stimulation therapy parameter for the program of the program group that contributes the greatest proportion of the energy consumption estimate.

18. The method of claim 15, wherein the certain level represents a predetermined consistent level of energy consumption.

19. The method of claim 15, wherein the energy consumption estimate rises above the certain level when an estimated time until a recharge is required drops below a predetermined period of time.

20. The method of claim 15, further comprising estimating, with the processor, a future drain on the power source, based on an association between the selected stimulation therapy parameters and historical usage of actual therapy parameters due to manual patient therapy adjustments, to determine the energy consumption estimate.

21. The method of claim 15, further comprising estimating, with the processor, a future drain on the power source using a record of patient postures and therapy parameters associated with the patient postures to determine the energy consumption estimate.

22. The method of claim 15, wherein the one or more recommended programming options are selected from a group consisting of:
reducing stimulation current amplitude;
reducing stimulation voltage amplitude;
reducing stimulation pulse rate;
reducing stimulation duty cycle;
altering stimulation pulse width;
altering a number of activated leads or electrodes;
altering an electrode combination;
altering electrode polarity;
altering a number of active programs in a program group; and
altering a program selected for a slot of a program group.

23. The method of claim 15, further comprising receiving, with a telemetry module of the programmer, the energy consumption estimate from the implantable medical device.

24. A system comprising:
means for delivering a stimulation therapy to a patient;
means for receiving user input corresponding to selected stimulation therapy parameters for delivering the stimulation therapy to the patient;
means for determining an energy consumption estimate of a power source based on the selected stimulation therapy parameters;
means for determining that the energy consumption estimate is above a certain level;
means for determining, in response to the means for determining that the energy consumption estimate is above the certain level, a respective value of a stimulation therapy parameter of the selected stimulation therapy parameters that causes a greatest amount of energy consumption of the selected stimulation parameters;
means for determining one or more programming options for altering the respective value of the stimulation therapy parameter to reduce the energy consumption estimate of the power source based on the selected stimulation therapy parameters;
means for presenting a recommendation of more than one of the one or more determined programming options to reduce the energy consumption estimate to the user with an indication that user selection of one or more of the recommended programming options would alter the respective value of the stimulation therapy parameter to reduce the energy consumption estimate; and
means for receiving user input, with the user interface, selecting one or more of the recommended programming options to reduce the energy consumption estimate presented via the user interface.

25. A non-transitory computer-readable medium comprising instructions that, upon execution, cause a processor to:
determine an energy consumption estimate for selected stimulation therapy parameters for delivering medical therapy to a patient with an implantable medical device;
determine that the energy consumption estimate is above a certain level;
determine, in response to the determining that the energy consumption estimate is above the certain level, a respective value of a stimulation therapy parameter of the selected stimulation therapy parameters that causes a greatest amount of energy consumption of the selected stimulation parameters;
determine one or more programming options for altering the respective value of the stimulation therapy parameter to reduce the energy consumption estimate of the power source based on the selected stimulation therapy parameters,
present, via a user interface, a recommendation of more than one of the one or more determined programming options to reduce the energy consumption estimate to a user with an indication that user selection of one or more of the recommended programming options would alter the respective value of the stimulation therapy parameter to reduce energy consumption of the implantable medical device; and
receive user input, with the user interface, selecting one or more of the recommended programming options to reduce the energy consumption estimate presented via the user interface.

26. The computer-readable medium of claim 25, wherein the computer-readable medium comprises instructions that, upon execution, cause the processor to estimate a future drain on a power source using a record of manual patient therapy parameter adjustments to determine the energy consumption estimate.

27. The computer-readable medium of claim 25, wherein the computer-readable medium comprises instructions that, upon execution, cause the processor to estimate a future drain on a power source using a record of patient postures and therapy parameters associated with the patient postures to determine the energy consumption estimate.

28. The computer-readable medium of claim 25, wherein the one or more recommended programming options are selected from a group consisting of:
reducing stimulation current amplitude;
reducing stimulation voltage amplitude;

reducing stimulation pulse rate;
reducing stimulation duty cycle;
altering stimulation pulse width;
altering a number of activated leads or electrodes;
altering an electrode combination;
altering electrode polarity;
altering a number of active programs in a program group; and
altering a program selected for a slot of a program group.

* * * * *